US008915839B2

(12) United States Patent
Mitsuhashi

(10) Patent No.: US 8,915,839 B2
(45) Date of Patent: Dec. 23, 2014

(54) IN-VIVO INFORMATION ACQUIRING SYSTEM

(75) Inventor: Kei Mitsuhashi, Nishltokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1203 days.

(21) Appl. No.: 12/199,645

(22) Filed: Aug. 27, 2008

(65) Prior Publication Data

US 2009/0062613 A1    Mar. 5, 2009

(30) Foreign Application Priority Data

Aug. 31, 2007    (JP) .................................. 2007-226972

(51) Int. Cl.
*A61B 1/04*    (2006.01)
*A61B 1/00*    (2006.01)

(52) U.S. Cl.
CPC ............. *A61B 1/041* (2013.01); *A61B 1/00016* (2013.01); *A61B 1/00179* (2013.01); *A61B 1/00009* (2013.01)
USPC ............................. 600/118; 600/103; 600/117

(58) Field of Classification Search
USPC ........................... 600/103, 109, 117, 118, 160
See application file for complete search history.

(56) References Cited

U.S. PATENT DOCUMENTS

| 3,749,831 | A | * | 7/1973 | Simpkins ...................... 348/460 |
| 4,893,306 | A | * | 1/1990 | Chao et al. .................... 370/458 |
| 5,712,689 | A | * | 1/1998 | Yasuki et al. ................. 348/561 |
| 6,573,919 | B2 | * | 6/2003 | Benear et al. ................. 347/116 |
| 7,647,604 | B2 | * | 1/2010 | Ramaswamy .................... 725/9 |
| 7,683,926 | B2 | * | 3/2010 | Schechterman et al. ........ 348/42 |
| 7,751,586 | B2 | * | 7/2010 | Matsubara .................... 382/100 |
| 8,320,606 | B1 | * | 11/2012 | Moorer ........................ 382/100 |
| 2004/0199061 | A1 | | 10/2004 | Glukhovsky et al. |
| 2005/0049461 | A1 | * | 3/2005 | Honda et al. .................. 600/160 |
| 2005/0177662 | A1 | * | 8/2005 | Hauke et al. .................. 710/104 |
| 2007/0006275 | A1 | * | 1/2007 | Wright et al. ................. 725/133 |
| 2007/0055099 | A1 | * | 3/2007 | Kimoto ........................ 600/109 |
| 2007/0118017 | A1 | | 5/2007 | Honda |

(Continued)

FOREIGN PATENT DOCUMENTS

| JP | 2001-231186 | | 8/2001 | |
| JP | 2006-304885 | | 11/2006 | |
| WO | WO 2007/026713 | * | 3/2007 | ............... A61B 1/00 |
| WO | WO 2007/029820 | * | 3/2007 | ............... A61B 1/00 |

OTHER PUBLICATIONS

Extended Supplementary European Search Report dated Oct. 1, 2014 from related European Patent Application No. 08 82 8087.0.

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An in-vivo information acquiring system previously sets synchronization signals for each imaging unit which captures an image. In the in-vivo information acquiring system, a capsule endoscope transmits scan-line data of an image to be transmitted using the synchronization signal corresponding to the imaging unit which captures the image to be transmitted, and a receiving apparatus identifies that the received scan-line data forms the image captured by the imaging unit corresponding to the detected synchronization signal by detecting the synchronization signal from received information.

4 Claims, 19 Drawing Sheets

(56) References Cited

U.S. PATENT DOCUMENTS

| | | | |
|---|---|---|---|
| 2007/0120976 A1* | 5/2007 | Matsumoto et al. | 348/71 |
| 2007/0252893 A1* | 11/2007 | Shigemori | 348/65 |
| 2008/0074491 A1* | 3/2008 | Matsui | 348/65 |
| 2008/0318541 A1* | 12/2008 | Kimoto | 455/277.1 |
| 2009/0051762 A1* | 2/2009 | Shigemori et al. | 348/65 |
| 2009/0076352 A1* | 3/2009 | Fujita et al. | 600/302 |
| 2009/0118585 A1* | 5/2009 | Honda et al. | 600/160 |
| 2009/0309860 A1* | 12/2009 | Hsu et al. | 345/211 |

* cited by examiner

FIG.9

| | PREAMBLE | VD | DUMMY | IMAGE | | L011-1 |
|---|---|---|---|---|---|---|
| | H BLANK | HD | DUMMY | IMAGE | | L011-2 |
| | H BLANK | HD | DUMMY | IMAGE | | L011-3 |
| | H BLANK | HD | DUMMY | IMAGE | | |
| | H BLANK | HD | DUMMY | IMAGE | | |
| G011 | H BLANK | HD | DUMMY | IMAGE | | ⋮ |
| | H BLANK | HD | DUMMY | IMAGE | | |
| | H BLANK | HD | DUMMY | IMAGE | | |
| | H BLANK | HD | DUMMY | IMAGE | | |
| | H BLANK | HD | DUMMY | IMAGE | | L011-(n-1) |
| | H BLANK | HD | DUMMY | IMAGE | UNIQUE INFORMATION11 | L011-n |
| | PREAMBLE | VD | DUMMY | IMAGE | | L021-1 |
| | H BLANK | HD | DUMMY | IMAGE | | L021-2 |
| | H BLANK | HD | DUMMY | IMAGE | | L021-3 |
| | H BLANK | HD | DUMMY | IMAGE | | L021-4 |
| G021 | H BLANK | HD | DUMMY | IMAGE | | L021-5 |
| | H BLANK | HD | DUMMY | IMAGE | | L021-6 |
| | H BLANK | HD | DUMMY | IMAGE | | |
| | H BLANK | HD | DUMMY | IMAGE | | ⋮ |
| Y021 | H BLANK | HD | DUMMY | IMAGE | | |
| | H BLANK | HD | DUMMY | IMAGE | | L021-(n-1) |
| | H BLANK | HD | DUMMY | IMAGE | UNIQUE INFORMATION21 | L021-n |

CANNOT BE ACQUIRED

FIG.13

| SYNCHRONIZATION SIGNAL / IMAGING UNIT | OBSERVATION IMAGE | | CORRECTION IMAGE T3 | |
|---|---|---|---|---|
| | VD | HD | VD | HD |
| FIRST IMAGING UNIT | VD1 | HD1 | VD01 | HD01 |
| SECOND IMAGING UNIT | VD2 | HD2 | VD02 | HD02 |

FIG.17
| VD | HD | IMAGING UNIT | LIGHT-ADJUSTMENT CONDITION | FRAME RATE |
|---|---|---|---|---|
| VD1 | HD1 | FIRST IMAGING UNIT | C | a |
| VD2 | HD2 | | | b |
| VD3 | HD3 | | | c |
| VD4 | HD4 | | D | a |
| VD5 | HD5 | | | b |
| VD6 | HD6 | | | c |
| VD7 | HD7 | SECOND IMAGING UNIT | C | a |
| VD8 | HD8 | | | b |
| VD9 | HD9 | | | c |
| VD10 | HD10 | | D | a |
| VD11 | HD11 | | | b |
| VD12 | HD12 | | | c |
T5
FIG.18
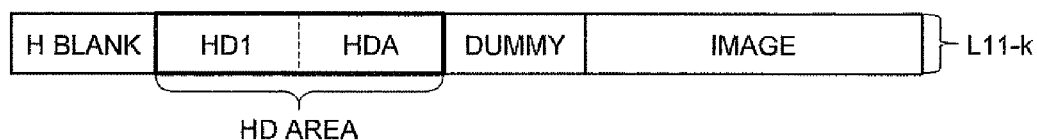
FIG.19
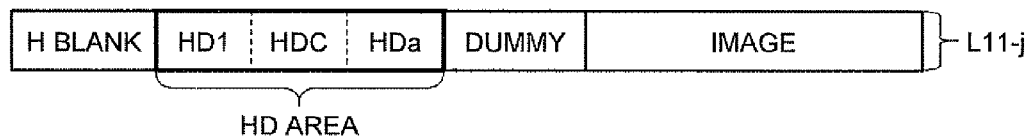

IN-VIVO INFORMATION ACQUIRING SYSTEM

CROSS-REFERENCE TO RELATED APPLICATIONS

This application is based upon and claims the benefit of priority from Japanese Patent Application No. 2007-226972, filed Aug. 31, 2007, the entire contents of which are incorporated herein by reference.

BACKGROUND OF THE INVENTION

1. Field of the Invention

The present invention relates to an in-vivo information acquiring system which acquires information inside a subject.

2. Description of the Related Art

Recently, a swallowable capsule endoscope has been developed in a field of endoscope. The capsule endoscope has an imaging function and a wireless transmission function. The capsule endoscope is introduced from a mouth of a patient for observing a body cavity, and sequentially picks up body cavity images of organs such as an esophagus, a stomach, and a small intestine moving with peristalsis until naturally excreted (e.g., see Japanese Patent Application Laid-Open No. 201-231186).

Image data which is captured inside a body by the capsule endoscope moving through the body cavity is transmitted to an outside of body via wireless transmission. Then, the image data is stored in a memory arranged in a receiving apparatus outside the body. Doctors and nurses can make a diagnosis using images displayed on a display based on the image data stored in the memory.

The common capsule endoscope described above used to be a monocular capsule endoscope which captures body cavity images in a forward direction of movement. Recently, however, a binocular capsule endoscope which captures images in both forward and backward directions of movement for widening a visual field and the like has been proposed (e.g., see US Patent Application Laid-Open 2004/199061). The binocular capsule endoscope has a structure where plural imaging units each of which has a pair of imaging devices such as an LED for illuminating a body cavity and a CCD for capturing body cavity images are arranged at both front and rear ends of the capsule endoscope to capture the images in a direction of movement of the capsule endoscope inside the body cavity.

A capsule endoscope system wirelessly transmits the image data captured by the capsule endoscope, for example, in a data structure similar to that of NTSC transmission of image. Specifically, the capsule endoscope processes the image captured by each imaging unit by a unit of scan-line data. The capsule endoscope wirelessly transmits first scan-line data using a vertical synchronization signal, and each following scan-line data using a horizontal synchronization signal. Further, the capsule endoscope transmits last scan-line data to which unique information indicating the imaging unit that has captured the image is attached, thereby finishing transmitting data corresponding to the single image. Receiving the entire scan-line data, the receiving apparatus processes the unique information attached to the last scan-line data, and identifies which imaging unit has captured the image formed by the series of received scan line data. Thus, the receiving apparatus receives the single image.

SUMMARY OF THE INVENTION

An in-vivo information acquiring system according to an aspect of the present invention includes a body-insertable apparatus which is introduced inside a subject and transmits a wireless-transmission signal including acquired in-vivo information to an outside and a receiving apparatus which receives the transmission signal transmitted from the body-insertable apparatus. The body-insertable apparatus includes a transmission-side storage unit which stores a synchronization signal previously set for each piece of attached information attached to the in-vivo information, a transmission unit which acquires from the synchronization signals stored in the transmission-side storage unit a synchronization signal corresponding to attached information that needs to be attached to the in-vivo information to be transmitted, and which transmits the in-vivo information to be transmitted using the acquired synchronization signal. The receiving apparatus includes a reception-side storage unit which stores a synchronization signal previously set for each piece of attached information attached to the in-vivo information, a detection unit which detects a synchronization signal from the receiving information, a processing unit which acquires attached information corresponding to a synchronization signal, of the synchronization signals stored in the reception-side storage unit, that is identical with the synchronization signal detected by the detection unit as attached information of the received in-vivo information.

The above and other objects, features, and advantages of this invention will be better understood by reading the following detailed description of presently preferred embodiments of the invention, when considered in connection with the accompanying drawings.

BRIEF DESCRIPTION OF THE DRAWINGS

FIG. 9 is an explanatory diagram of an image-signal component transmitted from a conventional capsule endoscope;

FIG. 13 is a table of illustration of correspondence among each imaging unit, each image, and each synchronization signal in the capsule endoscope shown in FIG. 1;

FIG. 17 is a table of illustration of correspondence among each imaging unit, each light-adjustment condition, each frame rate, and each synchronization signal in the capsule endoscope shown in FIG. 1;

FIG. 18 is an explanatory diagram of an example of scan-line data transmitted from the capsule endoscope shown in FIG. 1;

FIG. 19 is an explanatory diagram of an example of the scan-line data transmitted from the capsule endoscope shown in FIG. 1;

DETAILED DESCRIPTION OF THE PREFERRED EMBODIMENTS

Figure 1:
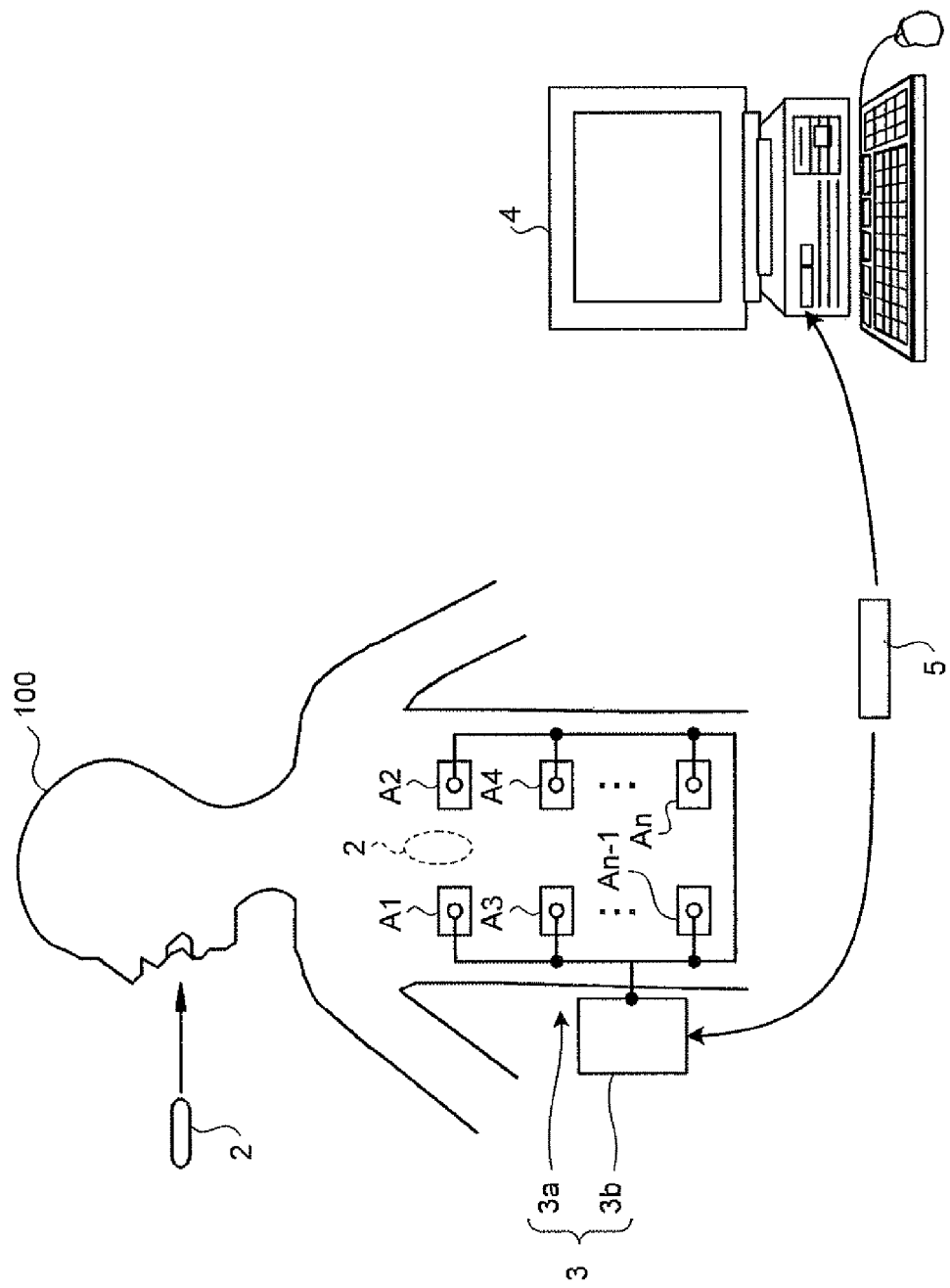
FIG. 1 is a schematic diagram of an overall configuration of an in-vivo information acquiring system according an embodiment.

Exemplary embodiments (referred to below as "embodiment", simply) of a wireless-transmission in-vivo information acquiring system and a body-insertable apparatus of the present invention are described below with reference to drawings. The present invention, however, is not limited to the embodiment. Same numerals are attached to identical components in the drawings.

The embodiment of the present invention is described. FIG. 1 is a schematic diagram of an overall configuration of a wireless-transmission in-vivo information acquiring system. The in-vivo information acquiring system employs a binocular capsule endoscope as an example of the body-insertable apparatus. As shown in FIG. 1, the wireless-transmission in-vivo information acquiring system includes a capsule endoscope 2 which is introduced inside a subject 100 to capture body cavity images, and performs wireless data transmission of a video signal to a receiving apparatus 3, a receiving apparatus 3 which receives body cavity image data wirelessly transmitted from the capsule endoscope 2, a display apparatus 4 which displays the body cavity images according to the video signal received by the receiving apparatus 3, and a portable storage medium 5 which performs data transmission and reception between the receiving apparatus 3 and the display apparatus 4.

Further, the receiving apparatus 3 includes a wireless-transmission unit 3a which includes plural receiving antennas A1 to An attached to an outer body surface of the subject 100, a main receiving unit 3b which performs processes such as a process on wireless-transmission signal. These units are detachably connected via a connector and the like. Alternatively, each of the receiving antennas A1 to An may be attached to a jacket to be worn by the subject 100 so that the receiving antennas A1 to An can be attached to the subject 100 wearing the jacket. Further, in this case, the receiving antennas A1 to An may be detachably attached to the jacket.

The display apparatus 4 displays body cavity images captured by the capsule endoscope 2, and is realized as a workstation and the like which displays an image according to the data acquired via the portable storage medium 5. Specifically, the display apparatus 4 may be realized by a CRT display, a liquid crystal display, or the like for displaying an image thereon, or realized by a printer or the like for outputting an image to other mediums.

The portable storage medium 5 is realized by a compact flash (registered trademark) memory and the like. The portable storage medium 5 is detachably attached to the main receiving unit 3b and the display apparatus 4, and has a function to output or store information when attached to the main receiving unit 3b and the display apparatus 4. Specifically, the portable storage medium 5 is attached to the main receiving unit 3b while the capsule endoscope 2 moves through the body cavity of the subject 100, and stores therein the data transmitted from the capsule endoscope 2. After the capsule endoscope 2 is excreted from the subject 100, i.e., after the capturing inside the subject 100 is finished, the portable storage medium 5 is detached from the main receiving unit 3b to be attached to the display apparatus 4, where the stored data is read out by the display apparatus 4. The portable storage medium 5 is used for data reception and transmission between the main receiving unit 3b and the display apparatus 4, whereby the subject 100 can act freely while the body cavity images are captured, and time for data reception and transmission to the display apparatus 4 can be shortened. Alternatively, a storage apparatus built into the main receiving unit 3b instead may be used for the data reception and transmission between the main receiving unit 3b and the display apparatus 4, and the storage apparatus may be connected to the display apparatus via wire or wireless connection.

Figure 2:
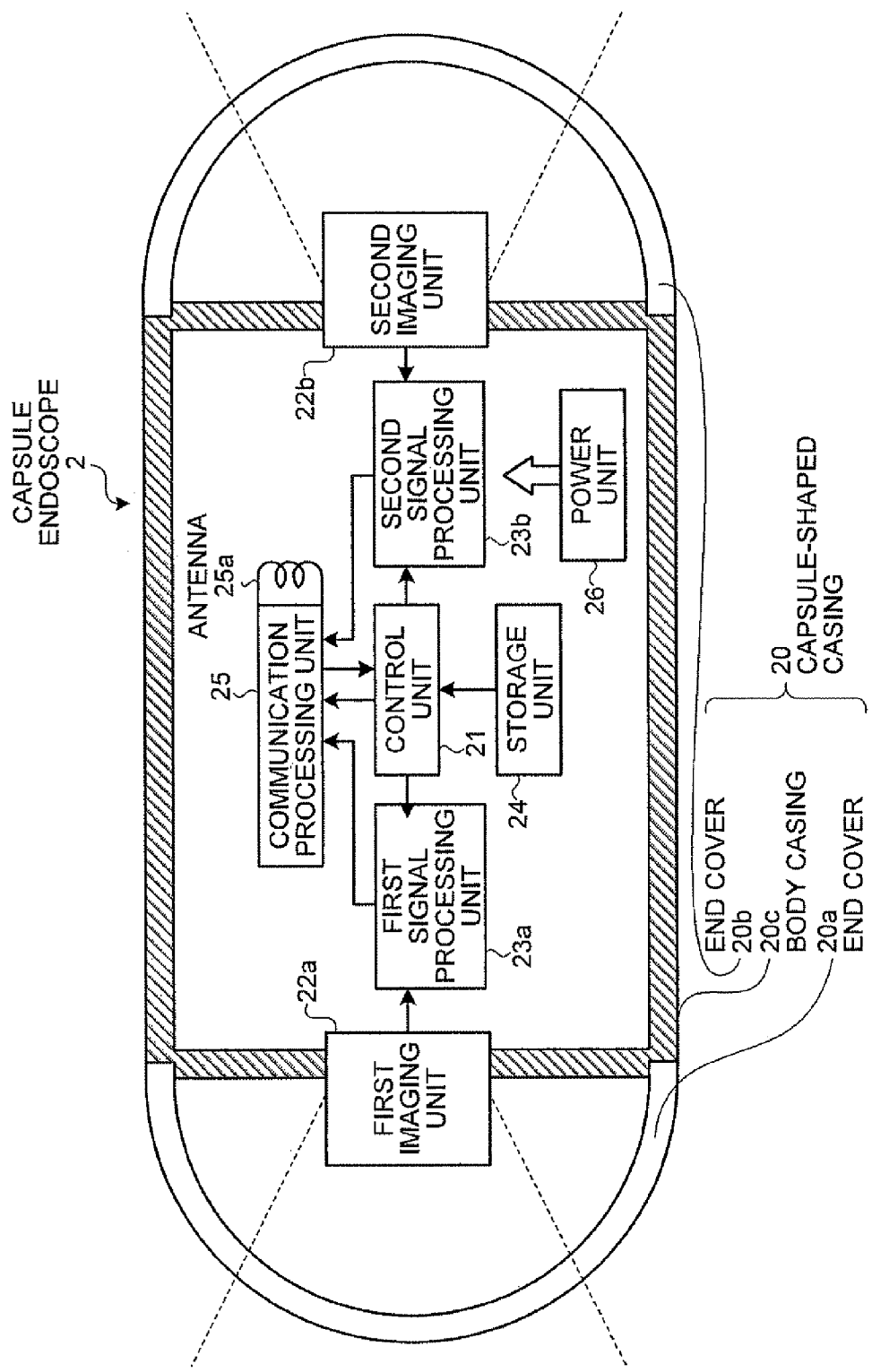
FIG. 2 is a block diagram of a configuration of a capsule endoscope shown in FIG. 1.

The configuration of the capsule endoscope 2, which is an example of the body-insertable apparatus according to the present invention, is described in detail below. FIG. 2 is a schematic diagram of a configuration of the capsule endoscope 2. As shown in FIG. 2, the capsule endoscope 2 includes inside a capsule-shaped casing 20 a first imaging unit 22a and a second imaging unit 22b which captured the body cavity images of the subject 100, and also includes a power unit 26 which supplies power for each component of the capsule endoscope 2.

The capsule-shaped casing 20 is formed with a dome-shaped transparent end cover 20a which covers the first imaging unit 22a, a dome-shaped transparent end cover 20b which covers the second imaging unit 22b, and a cylinder-shaped body casing 20c which is arranged to keep the end covers 20a, 20b and the body casing 20c watertight. The capsule-shaped casing 20 has a size which can be swallowed from a mouth of the subject 100. The end cover 20a is attached to a front end of the body casing 20c while the end cover 20b is attached to a rear end of the body casing 20c.

The body casing 20c is made of a color material which does not transmit visible light. The body casing 20c contains a control unit 21 which controls driving of each component of the capsule endoscope 2 and an input-output process of signals in each component, the first imaging unit 22a and the second imaging unit 22b which capture the inside of body cavity, a first signal processing unit 23a which processes the images captured by the first imaging unit 22a, a second signal processing unit 23b which processes images captured by the second imaging unit 22b, a storage unit 24 which stores information needed for wireless transmission, a communication processing unit 25 which modulates various signals transmitted to the display apparatus 4 arranged outside into wireless-transmission signals or demodulates the wireless-transmission signals received via an antenna 25a, and a power unit 26 which supplies driving power for each component of the capsule endoscope 2. The communication processing unit 25 has the antenna 25a which is a coiled antenna or the like, and which transmits and receives wireless transmission signals to/from an external antenna.

The first imaging unit 22a captures body cavity images of the subject 100. Specifically, the first imaging unit 22a is realized with an imaging device such as a CCD and a CMOS, and a light-emitting device such as an LED for illuminating an imaged field of the imaging device, and optical components such as a lens for forming an image based on reflected light of the imaging field to the imaging device. The first imaging unit 22a, which is fixated at a front end of the body casing 20c as described above, forms an image based on reflected light of the imaging field received through the end cover 20a to thereby capture the body cavity images of the subject 100.

The second imaging unit 22b, similarly to the first imaging unit 22a, captures body cavity images of the subject 100, and is realized with an imaging device such as a CCD and a CMOS, and a light-emitting device such as an LED for illuminating an imaged field of the imaging device, and optical components such as a lens for forming an image based on reflected light of the imaging field to the imaging device. The second imaging unit 22b, which is fixated at a rear end of the body casing 20c as described above, forms an image based on reflected light of the imaging field received through the end cover 20b to thereby capture the body cavity images of the subject 100.

In the capsule endoscope 2, each imaging unit transmits scan-line data of images using a synchronization signal having a unique signal constellation so that it can be identified which imaging unit captures the image, the first imaging unit 22a or the second imaging unit 22b.

The synchronization signal is a horizontal synchronization signal or a vertical synchronization signal. The signal constellations of each vertical synchronization signal and each horizontal synchronization signal are previously set corresponding to the first imaging unit 22a and the second imaging unit 22b which captures the image, respectively.

Figure 3:
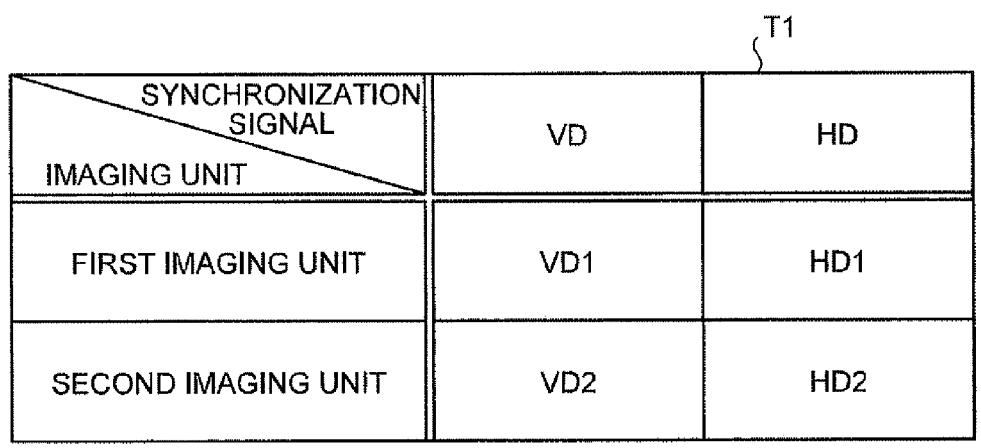
FIG. 3 is a table of illustration of correspondence between each imaging unit shown in FIG. 2 and each synchronization signal.

For example, as shown by a table T1 in FIG. 3, VD1 with a unique signal constellation indicating the first imaging unit 22a is previously set as the vertical synchronizing (VD) signal for the first imaging unit 22a, and HD1 with a unique signal constellation indicating the first imaging unit 22a is previously set as the horizontal synchronizing (HD) signal. Further, VD2 with a unique signal constellation, different from that of VD1, indicating the second imaging unit 22b is previously set as the VD signal of the second imaging unit 22b, and HD2 with a unique signal constellation, different from that of HD1, indicating the second imaging unit 22b is previously set as the HD signal. The storage unit 24 stores therein signal constellations of the VD signals and the HD signals previously set corresponding to each imaging unit shown in FIG. 3, respectively. The control unit 21 acquires synchronization signals corresponding to the first imaging unit 221 and the second imaging unit 22b from the synchronization signals stored in the storage unit 24, and outputs the acquired synchronization signals to the first imaging unit 22a and the second imaging unit 22b, respectively. The control unit 21 acquires VD1 as the VD signal of the synchronization signals corresponding to the first imaging unit 22a, and outputs VD1 to the first signal processing unit 23a. The control unit 21 acquires HD1 as the HD signal of the synchronization signals corresponding to the first imaging unit 22a, and outputs HD1 to the first signal processing unit 23a. Further, the control unit 21 acquires VD2 as the VD signal of the synchronization signals corresponding to the second imaging unit 22b, and outputs VD2 to the second signal processing unit 23b. The control unit 21 acquires HD2 as the HD signal of the synchronization signals corresponding to the second imaging unit 22b.

The first signal processing unit 23a processes the image captured by the first imaging unit 22a using the VD1 signal and HD1 signal output from the control unit 21 to thereby generate plural scan-line data as an image signal corresponding to the image.

Figure 4:
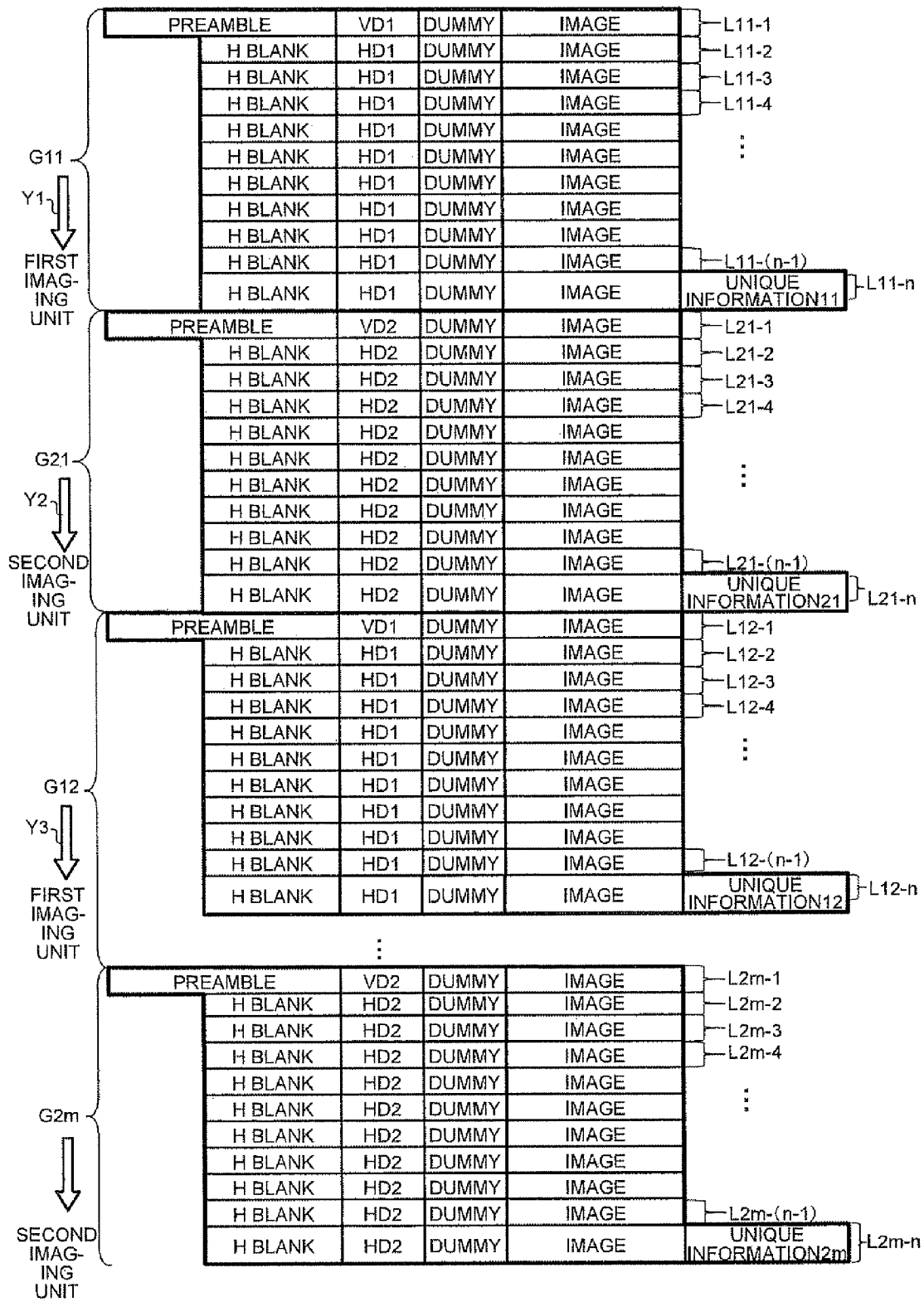
FIG. 4 is an explanatory diagram of an image signal transmission process in the capsule endoscope shown in FIG. 1.

Specifically, as shown in FIG. 4, the first signal processing unit 23a processes an image G11 captured by the first imaging unit 22a in units of scan-line data. Further, the first signal processing unit 23a sets VD1 corresponding to the first imaging unit 22a which has captured the image G11 as a vertical synchronization signal of a first scan-line data L11-1 of the image G11 to be transmitted. Further, the first signal processing unit 23a sets HD1 corresponding to the first imaging unit 22a which has captured the image G11 as a horizontal signal of each of scan-line data L11-2 to L11-n following the scan-line data to which VD1 is attached. Further, the first signal processing unit 23a attaches unique information 11 such as unique information, a white balance coefficient, a product serial number, product version information, and product type information of the first imaging unit 22a which has captured the image G11 to an end of a last scan-line data of the image G11. Further, the first signal processing unit 23a attaches a preamble signal indicating a beginning of the image signal to the first scan-line data. The first signal processing unit 23a attaches a dummy signal to a position between VD1 or HD1 and the scan-line data of the image signal, and attaches a horizontal blank (H blank) signal consisting of a predetermined number of bits to a position ahead of HD1, so that the receiving apparatus 3 can efficiently detect each signal.

Further, the second signal processing unit 23b processes an image captured by the second imaging unit 22b using the VD2 signal and the HD2 signal output from the control unit 21 to thereby generate plural scan-line data as an image signal corresponding to the image.

Specifically, as shown in FIG. 4, the second signal processing unit 23b processes an image G21 captured by the second imaging unit 22b in units of scan-line data. Further, the second signal processing unit 23b sets VD2 corresponding to the second imaging unit 22b which has captured the image G21 as a vertical synchronization signal of a first scan-line data L21-1 of the image G21 to be transmitted. Further, the second signal processing unit 23b sets HD2 corresponding to the second imaging unit 22b which has captured the image G21 as a horizontal signal of each of scan-line data L21-2 to L21-n following the scan-line data to which VD2 is attached. Further, the second signal processing unit 23b attaches unique information 21 such as unique information, a white balance coefficient, a product serial number, product version information, and product type information of the second imaging unit 22b which has captured the image G21 to an end of last scan-line data of the image G21. Further, the second signal processing unit 23a attaches a preamble signal indicating a beginning of the image signal to the first scan-line data. The second signal processing unit 23b attaches a dummy signal to a position between VD2 or HD2 and the scan-line data of the image signal, and attaches a horizontal blank (H blank) signal consisting of a predetermined number of bits to a position ahead of HD2.

Then, the communication processing unit 25 transmits each scan-line data using VD1, HD1, VD2, or HD2 set by the first signal processing unit 23a or the second signal processing unit 23b as the synchronization signal via the antenna 25a.

As a result, as shown in FIG. 4, for the image G11 captured by the first imaging unit 22a, the scan-line data L11-1 to L11-n using VD1 or HD1, which has a signal constellation that is unique for the first imaging unit 22a, are transmitted via the antenna 25a to the receiving apparatus 3 arranged outside. Then, for the image G21 captured by the second imaging unit 22b, the scan-line data L21-1 to L21-n using VD2 or HD2, which corresponds to the second imaging unit 22b, are transmitted via the antenna 25a. Further, for an image G12 captured by the first imaging unit 22a, scan-line data L12-1 to L12-n using the VD1 signal or the HD1 signal, which corresponds to the first imaging unit 22a, are transmitted via the antenna 25a. The unique information which is attached to each piece of image data may differ among the images as well as among the imaging units. FIG. 4 shows an example of a case where the unique information differs among images. There may be a case where the unique information is identical among plural images captured by a same imaging unit when the condition is adjusted for every predetermined number of images.

Thus, the capsule endoscope 2 sequentially transmits each scan-line data of the image captured by the first imaging unit 22a or the second imaging unit 22b to the receiving apparatus 3. The receiving apparatus 3 identifies which imaging unit has captured an image corresponding to the scan-line data based on each synchronization signal included in the information transmitted from the capsule endoscope 2.

Figure 5:
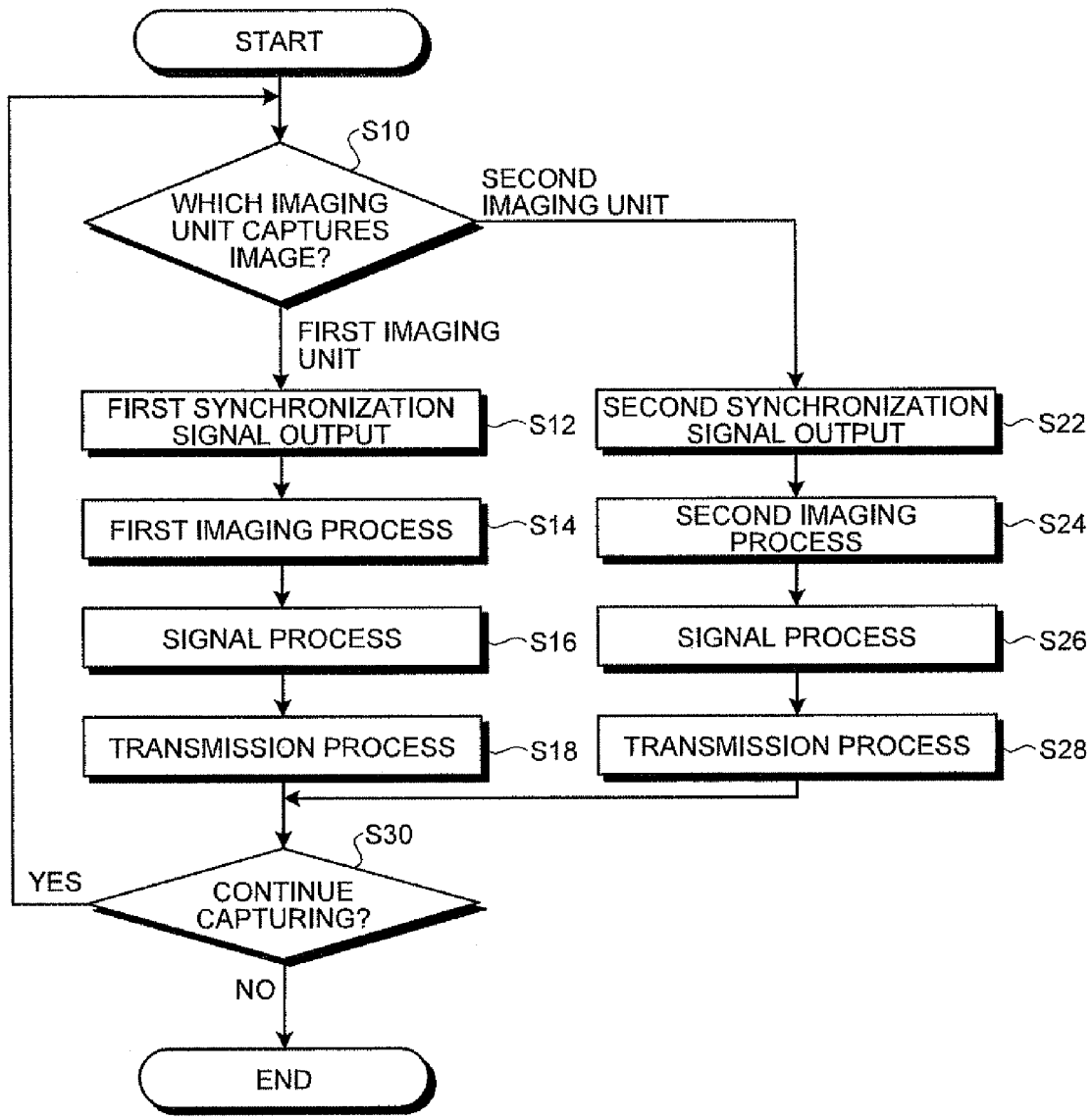
FIG. 5 is a flowchart of a procedure of an image-signal transmission process in the capsule endoscope shown in FIG. 2.

Next, an image-signal transmission process of the capsule endoscope 2 is described below with reference to FIG. 5. As shown in FIG. 5, the control unit 21 determines which imaging unit captures an inside of body cavity, the first imaging unit 22a or the second imaging unit 22b based on a predetermined process timing (Step S10).

When the control unit 21 determines that the first imaging unit 22a captures the inside of body cavity (Step S10: first imaging unit), the control unit 21 acquires a first synchronization signal corresponding to the first imaging unit 22a from the storage unit 24, and outputs the first synchronization signal to the first signal processing unit 23a (Step S12). The control unit 21 makes the first imaging unit 22a perform an imaging process to capture an body cavity image (Step S14). The first signal processing unit 23a processes single image captured by the first imaging unit 22a, and performs a signal processing to set the first synchronization signal on each scan-line data (Step S16). As described above, the first signal processing unit 23a sets, for example, VD1 on first scan-line data as a VD signal, and sets, for example, HD1 on other scan-line data as an HD signal. Then, the communication processing unit 25 sequentially modulates each scan-line data generated by the first signal processing unit 23a into wireless-transmission signals, and performs a transmission process to wirelessly transmit the wireless-transmission signals via the antenna 25a (Step S18).

On the other hand, when the control unit 21 determines that the second imaging unit 22b captures the inside of body cavity (Step S10: second imaging unit), the control unit 21 acquires a second synchronization signal corresponding to the second imaging unit 22b from the storage unit 24, and outputs the second synchronization signal to the second signal processing unit 23b (Step S22). The control unit 21 makes the second imaging unit 22b perform the imaging process to capture the body cavity image (Step S24). The second signal processing unit 23b processes single image captured by the second imaging unit 22b, and performs a signal process to set the second synchronization signal on each scan-line data (Step S26). As described above, the second signal processing unit 23b sets, for example, VD2 on first scan-line data as a VD signal, and sets, for example, HD2 on other scan-line data as an HD signal. Then, the communication processing unit 25 sequentially modulates each scan-line data generated by the second signal processing unit 23b into wireless-transmission signals, and performs a transmission process to wirelessly transmit the wireless-transmission signals via the antenna 25a (Step S28).

The control unit 21 determines, based on instruction information and the like transmitted from an outside, whether the capturing is to be continued (Step S30). When the control unit 21 determines that the capturing is not to be continued (Step S30: No), the control unit 21 stops the imaging process of each imaging unit. When the control unit 21 determines that the capturing is to be continued (Step S30: Yes), the control unit 21 returns to Step S10 and determines which imaging unit performs the imaging process.

Figure 6:
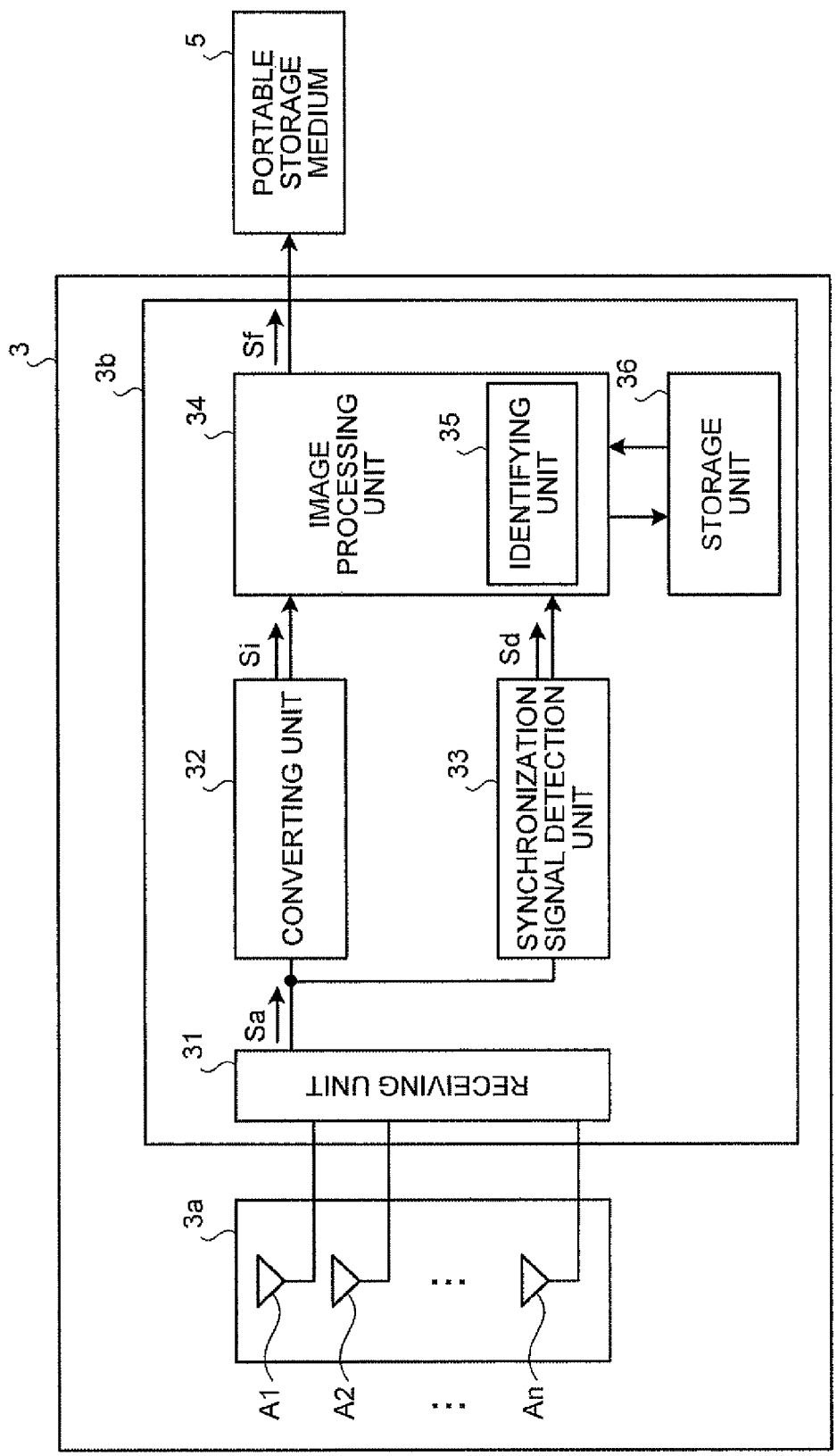
FIG. 6 is a block diagram of a configuration of a receiving apparatus shown in FIG. 1.

Next, the receiving apparatus shown in FIG. 1 is described with reference to FIG. 6. As shown in FIG. 6, the receiving apparatus 3 includes the wireless-transmission unit 3a which includes the receiving antennas A1 to An, and main receiving unit 3b which performs a process on a wireless-transmission signal received via the receiving antennas A1 to An and other processes. As shown in FIG. 6, the main receiving unit 3b includes a receiving unit 31, a converting unit 32, a synchronization signal detection unit 33, an image processing unit 34, and a storage unit 36.

The receiving unit 31 switches an antenna A used for receiving the wireless-transmission signal, and performs receiving processes such as a demodulation, and analog/digital conversion on the wireless-transmission signal received via the switched antenna A, and outputs a signal Sa. The converting unit 32 converts the signal Sa output from the receiving unit 31 into a signal Si which can be processed by the image processing unit 34. The converting unit 32 outputs the signal Si at a synchronizing-signal output timing of the synchronization signal detection unit 33.

Figure 7:
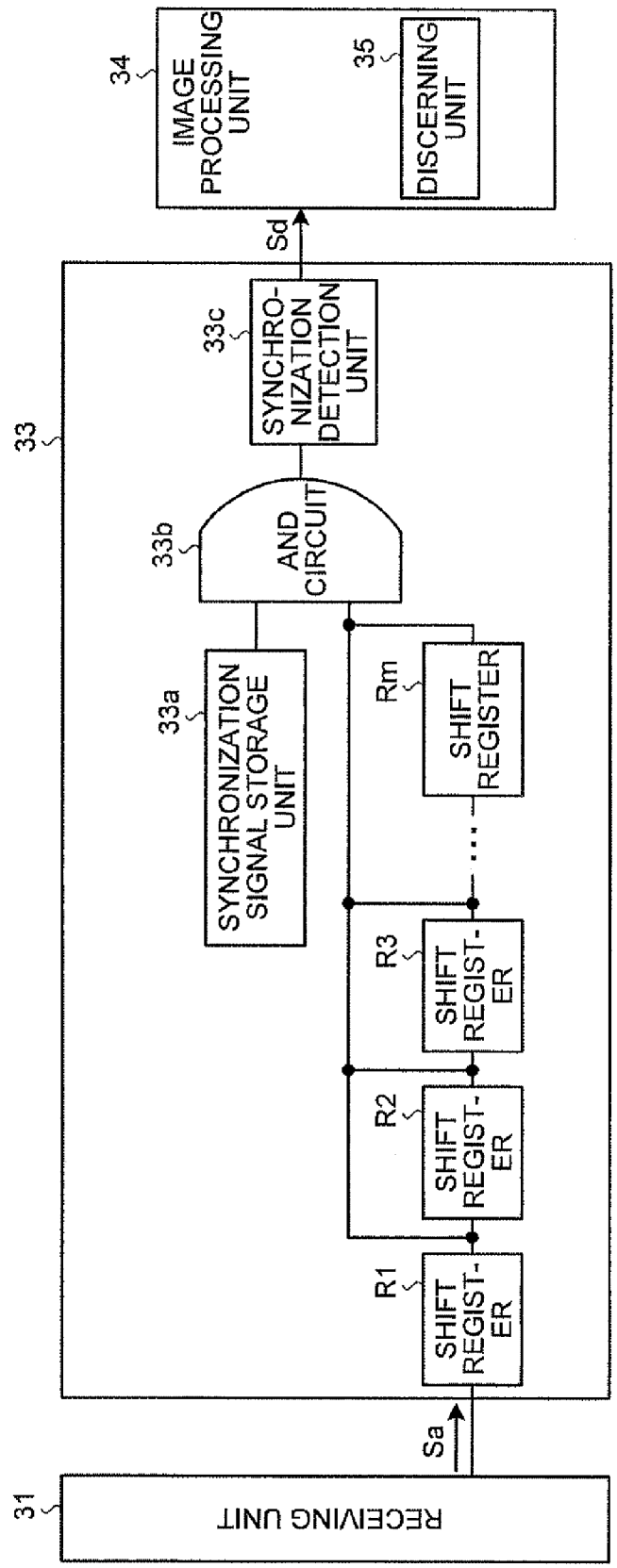
FIG. 7 is a block diagram showing a configuration of main parts of the receiving apparatus shown in FIG. 6.

The synchronization signal detection unit 33 detects various synchronization signals from the signal Sa, and outputs the synchronization signal information about the detected synchronization signal to the imaging processing unit. As shown in FIG. 7, the synchronization signal detection unit 33 includes a synchronizing-signal storage unit 33a, shift registers R1 to Rm, an AND circuit 33b, and a synchronization detection unit 33c.

The synchronizing-signal storage unit 33a stores each synchronization signal used in the capsule endoscope 2. The synchronizing-signal storage unit 33a stores, for example, signal codes of VD1, VD2, HD1, and HD2 shown in FIG. 3. The shift registers R1 to Rm output each signal value of the signal Sa which is input from the receiving unit 31 to the AND circuit 33b in order of input. There is a number of the shift registers R1 to Rm corresponding to a number of bits of each synchronization signal. When each signal of VD1, VD2, Hd1, and HD2 consists of m bits, m shift registers are arranged.

The AND circuit 33b compares a signal output from the shift registers R1 to Rm with a signal code of each synchronization signal stored in the synchronizing-signal storage unit 33a bit by bit. When the signal output from the shift registers R1 to Rm is identical with one of the synchronization signals stored in the synchronizing-signal storage unit 33a, the identical synchronization signal is transmitted to the synchronization detection unit 33c. The synchronization detection unit 33c outputs the synchronization signal which is output from the AND circuit 33b, to the image processing unit 34 along with the information indicating the scan-line data into which the synchronization signal is attached, as synchronization signal information Sd. Further, when a synchronization signal of following scan-line data is not output from the AND circuit 33b after a following synchronizing-signal-output timing of the scan-line data passes since the previous synchronizing-signal-output timing of scan-line data, the synchronization detection unit 33c determines that there is a transmission error in the scan-line data whose synchronization signal is not output. Further, the synchronization detection unit 33c adds information indicating that there is a transmission error into synchronizing-signal information Sd about the scan-line data.

The image processing unit 34 executes predetermined processing according to the sign Si output from the converting unit 32, and outputs the image data Sf corresponding to one frame image. The storage unit 36 stores the information required for image processing. The storage unit 36 stores the signal constellation of VD signal and HD signal that are preset respectively corresponding to each item of the image unit column exemplified in table 3 of FIG. 3.

The image processing unit 34 includes an identifying unit 35. The identifying unit 35 identifies whether an image formed by the received scan-line data is captured by the imaging unit corresponding to the synchronization signal, of each synchronization signal stored in the storage unit 36, that is identical with the synchronization signal detected by the synchronizing-signal detection unit 33. Further, based on the result of identifying, the image processing unit 34 processes the series of scan-line data captured by the same imaging unit, and outputs image data Sf corresponding to a frame of the images captured by the imaging unit.

Figure 8:
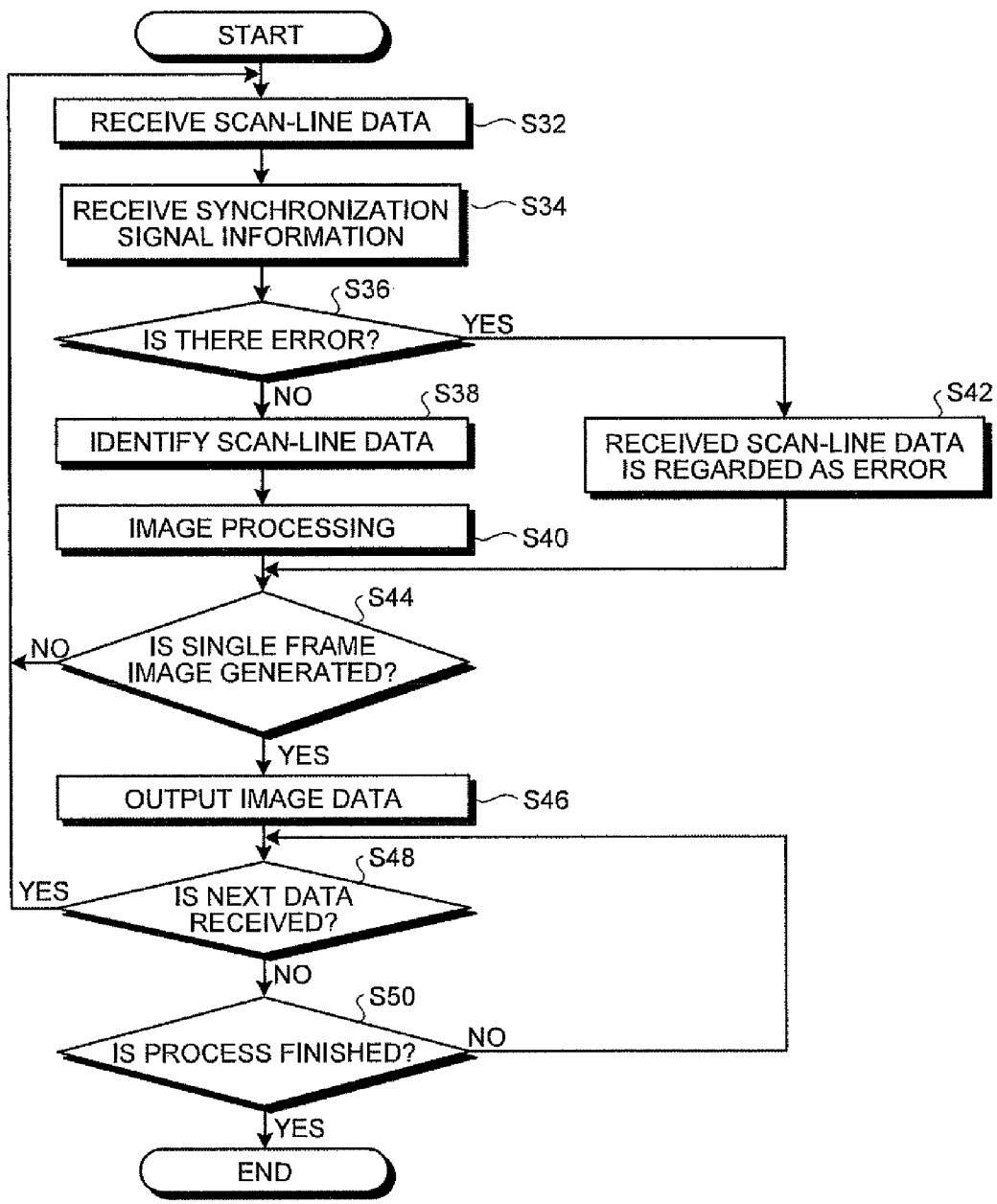
FIG. 8 is a flowchart of an image processing procedure in an image processing unit shown in FIGS. 6 and 7.

Next, the image processing of the image processing unit 34 is described with reference to FIG. 8. As shown in FIG. 8, the image processing unit 34 receives scan-line data to be processed from the converting unit 32 (Step S32), and receives synchronizing-signal information about the synchronizing-signal detection of the scan-line data (Step S34). Further, the image processing unit 34 determines whether there is an error such as a transmission error in the scan-line data to be processed which is received from the converting unit 32 based on the received synchronizing-signal information (Step S36).

When the image processing unit 34 determines that there is no error in the scan-line data (Step S36: No), the identifying unit 35 identifies an imaging unit corresponding to the scan-line data based on the received synchronizing-signal information (Step S38). After the identifying unit 35 identifies that the imaging unit corresponding to the scan-line data is identical with the imaging unit corresponding to image data, the image processing unit 34 performs an image processing on the scan-line data (Step S40).

On the other hand, when the image processing unit 34 determines that there is an error in the scan-line data to be processed (Step 36: Yes), the image processing unit 34 determines that the received scan-line data contains an error (Step S42), and does not perform any process on the scan-line data.

Further, after the process at Step S40 finishes, or after the determination of error at the Step S42 finishes, the image processing unit 34 determines whether a single-frame image is generated through the image processing (Step S44). When the image processing unit 34 determines that the single-frame image is not generated (Step S44: No), the image processing unit 34 proceeds to Step S32 to receive next scan-line data and repeat the processes. On the other hand, when the image processing unit 34 determines that the single frame image is generated (Step S44: Yes), the image processing unit 34 outputs the generated image data of a single frame to the portable storage medium 5 or the storage unit 36 along with the unique information of the imaging unit which has captured the image (Step S46). In this case, the image processing unit 34 may compress the generated image data and output the same. Further, the image processing unit 34 determines whether next scan-line data is to be received (Step S48). When the image processing unit 34 determines that the next scan-line data is to be received (Step S48: Yes), the image processing unit 34 proceeds to Step S32 and continues the processes. On the other hand, when the image processing unit 34 determines that the next scan-line data is not to be received (Step S48: No), the image processing unit 34 determines whether the process is finished based on instruction information input from an outside and other information (Step S50). When the image processing unit 34 determines that the process is finished (Step S50: Yes), the image processing unit finishes the image processing. When the image processing unit 34 determines that the process is not finished (Step S50: No), the image processing unit 34 returns to Step S48 and determines whether the next scan-line data is to be received.

The identifying process on each scan-line data is described taking a case shown in FIG. 4 as an example. The image processing unit 34 receives the scan-line data L11-1 from the converting unit 32, and receives the synchronizing-signal information Sd including the synchronization signal VD1 of the scan-line data L11-1 detected by the synchronizing-signal detection unit 33. The identifying unit 35 identifies that the scan-line data L11-1 transmitted using VD1 is scan-line data of an image captured by the first imaging unit 22a referring to the table T1 stored in the storage unit 36. Then, the image processing unit 34 receives the scan-line data L11-2 from the converting unit 32, and receives the synchronizing-signal information Sd including the synchronization signal HD1 of the scan-line data L11-2 detected by the synchronizing-signal detection unit 33. The identifying unit 35 identifies that the scan-line data L11-2 transmitted using HD1 is the scan-line data of the image captured by the first imaging unit 22a referring to the table T1 stored in the storage unit 36. Thus, the identifying unit 35 identifies that each scan-line data L11-1 to L11-n is the scan-line data of the image captured by the first imaging unit 22a based on the synchronizing-signal information Sd which is sequentially received by the image processing unit 34. Further, as shown by an arrow Y1, the image processing unit 34 processes the series of scan-line data L11-1 to L11-n, which have been identified by the identifying unit 35 as the scan-line data of the image captured by the first imaging unit 22a, to generate the image G11.

Similarly, for the image G21, the identifying unit 35 identifies that the scan-line data L21-1 is scan-line data of an image captured by the second imaging unit 22b based on the fact that VD2 is detected by synchronizing-signal detection unit 33 as the VD signal of the scan-line data L21-1. Further, the identifying unit 35 identifies that the scan-line data L21-2 is the scan-line data of the image captured by the second imaging unit 22b based on the fact that HD2 is detected by the synchronizing-signal detection unit 33 as the HD signal of the scan-line data L21-2. The identifying unit 35 identifies that the scan-line data L21-1 to L21-n are the scan-line data of the image captured by the second imaging unit 22b based on the synchronizing-signal information Sd which is sequentially received by the image processing unit 34. Further, as shown by an arrow Y2, the image processing unit 34 processes the series of scan-line data L21-1 to L21-n, which have been identified by the identifying unit 35 as the scan-line data of the image captured by the second imaging unit 22b, to generate the image G21. Similarly, the scan-line data L21-1 to L12-n to which VD1 or HD1 corresponding to the first imaging unit 22a is attached are determined to correspond to the first imaging unit 22a. Then, as shown by an arrow Y3, the image processing unit 34 processes the scan-line data L12-L12-n to generate the image G12.

In case of conventional capsule endoscopes having plural imaging units, unique information indicating an imaging unit which has captured the image is attached only to last scan-line data instead of each scan-line data, and the scan-line data is thus transmitted so that the amount of data transmission can be reduced. Further, the receiving apparatus processes the unique information attached to the last scan-line data after receiving all scan-line data, and identifies which imaging unit of the capsule endoscope has captured an image formed by the series of received scan-line data, to thereby obtain single image.

Therefore, conventionally, even when a receiving apparatus receives each scan-line data to form single image, the unique information may not be acquired due to a data error which occurs in a part of the unique information during the wireless transmission. In such a case, the receiving apparatus cannot identify which imaging unit of the capsule endoscope has captured the image formed by the series of received scan-line data, and thus cannot output the image. The image as a whole is regarded as an error.

On the other hand, in the present embodiment, the capsule endoscope 2 transmits the scan-line data using the VD signal or the HD signal having a signal constellation which is unique for each imaging unit so that the receiving apparatus can identify which imaging unit has captured the image. Further, for every scan-line data, the receiving apparatus 3 identifies which imaging unit of the plural imaging units of the capsule endoscope 2 has captured the image corresponding to scan-line data based on the VD signal or the HD signal detected from the received scan-line data, and then the scan-line data is processed. Thus, the receiving apparatus 3 can identify which imaging unit has captured the image of the scan-line data for every scan-line data, whereby even when the unique information is not acquired because there is a data error or the like in the part of the unique information which occurs during the wireless transmission, the whole image is not regarded as an error, and the receiving apparatus can securely identify the series of scan-line data captured by the same imaging unit to generate single image.

Further, conventionally, the unique information is transmitted only once for single image. When a transmission error or the like occurs during the transmission of the unique information, the receiving apparatus cannot identifies which imaging unit of the capsule endoscope has captured an image corresponding to the plural received scan-line data, and thus cannot generate the image even when all image information but the unique information is acquired. Therefore, conventionally, when the transmission error or the like occurs during the transmission of the unique information, the whole image is naturally regarded as an error. Specifically, as shown in FIG. 9, when the transmission error occurs during the transmission of the unique information 21 of an image G021 transmitted after an image G011 and the receiving apparatus does not acquire an imaging-unit-identification signal of the unique information 21, the receiving apparatus cannot identify which imaging unit of the capsule endoscope has captured the image corresponding to scan-line data L021-1 to L021-n transmitted previous to the scan-line data, and the receiving apparatus ends up regarding the whole image G021 as an error and cannot acquire the image G021.

Figure 10:
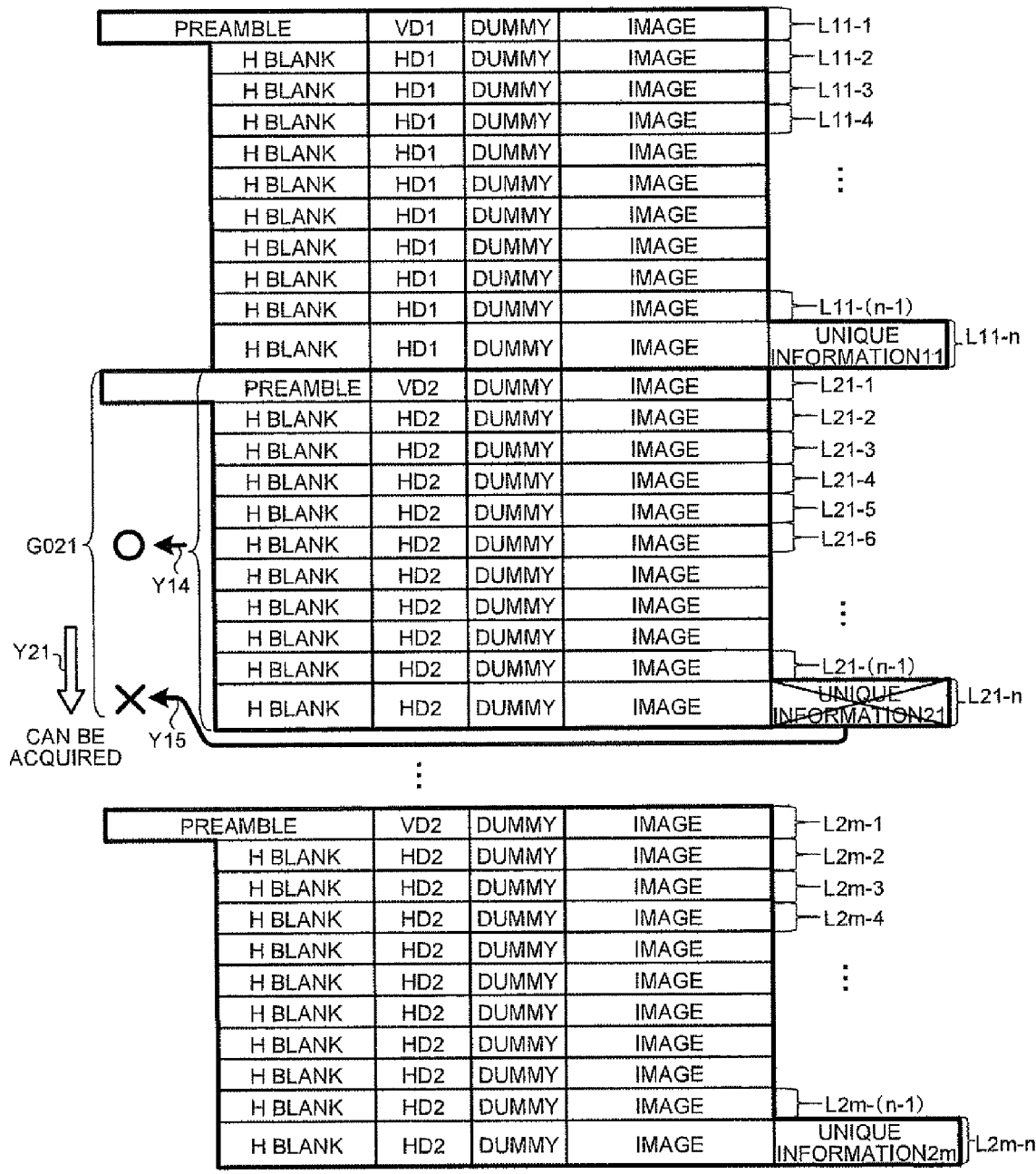
FIG. 10 is an explanatory diagram of the image-signal component transmitted from the capsule endoscope shown in FIG. 1.

On the other hand, in the present embodiment, the capsule endoscope 2 transmits the scan-line data using the VD signal or the HD signal having the signal constellation unique for each imaging unit so that the receiving apparatus 3 can identify which imaging unit has captured the image. Thus, as shown in FIG. 10, even when the receiving apparatus 3 cannot acquire the unique information 21 of the scan-line data L21-n as shown by an arrow Y15 due to a transmission error which occurs during the transmission of the unique information 21 of the image G021, the receiving apparatus 3 detects HD2 in the scan-line data L21-1 to L21-n transmitted previous to the scan-line data L21-1 so that the receiving apparatus 3 can identify that each scan-line data L21-1 to L21-n is captured by the second imaging unit 22b of the capsule endoscope 2 as shown by an arrow Y14.

As a result, as shown by an arrow Y21, the receiving apparatus 3 does not regard the whole image G021 as an error, and can acquire the image G021 by processing the scan-line data L21-1 to L21-n but the data of unique information 21 where the transmission error occurs. Further, the image processing unit 34 or the display apparatus 4 may store or display the image G021 by supplementing an area corresponding to the unique information 21 of the image G021 with data of the scan-line data L21-1 to L21-n transmitted previous to the unique information 21.

Thus, in the present embodiment, the capsule endoscope 2 transmits the scan-line data of the image using the synchronization signal corresponding to the imaging unit which has captured the image to be transmitted so that the receiving apparatus 3 can identify which imaging unit has captured the image. The receiving apparatus 3 can identify which imaging unit has captured the image corresponding to each piece of received information based on the synchronization signal for ever scan-line data. As a result, according to the present embodiment, even when the receiving apparatus 3 cannot accurately receive the whole transmitted data due to the transmission error which occurs during the transmission of the image data, the receiving apparatus can identify which imaging unit has captured the image corresponding to each scan-line data other than the scan-line data where the error occurs, and thus can acquire transmitted data corresponding to single image.

Further, although the capsule endoscope having two imaging units is described as the in-vivo information acquiring system, predetermined synchronization signals corresponding to each imaging unit may be naturally used for a capsule endoscope having more than two units. Further, in the present embodiment, the capsule endoscope is not limited to a capsule endoscope having plural imaging units. The present embodiment may be applied to the in-vivo information acquiring system including a capsule endoscope having single imaging unit.

For example, for the capsule endoscope having single imaging unit, a case where the imaging unit captures the observation image for observing an inside of the subject 100, and the correction image for correcting the observation image. A storage unit of the capsule endoscope and a storage unit of the receiving apparatus store therein synchronization signals previously set for intended usages of each image. Further, in the capsule endoscope, a signal processing unit and a communication processing unit transmit scan-line data of an image to be transmitted using a synchronization signal, of the synchronization signals stored in the storage unit, that corresponds to an intended usage of the image to be transmitted. Further, in the receiving apparatus, a synchronizing-signal detection unit detects the synchronization signal from the received scan-line data, and the image processing unit acquires the intended usage corresponding to the synchronization signal, of the synchronization signals stored in the storage unit, that is identical with the synchronization signal detected by the synchronizing-signal detection unit as the intended usage of the image formed by the scan-line data to thereby generate the image based on the scan-line data.

Figure 11:
FIG. 11 is a table of illustration of correspondence between each image captured by the capsule endoscope according the embodiment and each synchronization signal.

For example, as shown by a table T2 in FIG. 11, VD1 having a signal constellation unique for an ordinary observation image is set as a VD signal of the ordinary observation image, and HD1 having the signal constellation unique for the ordinary observation image is set as an HD signal of the ordinary observation image. Further, VD0 having the signal constellation unique for the correction image is set as the VD signal of the correction image, and HD0 having the signal constellation unique for the correction image is set as the HD signal of the correction image. The table T2 illustrated in FIG. 11 is stored in the storage unit of the capsule endoscope, and the storage unit of the receiving apparatus.

Figure 12:
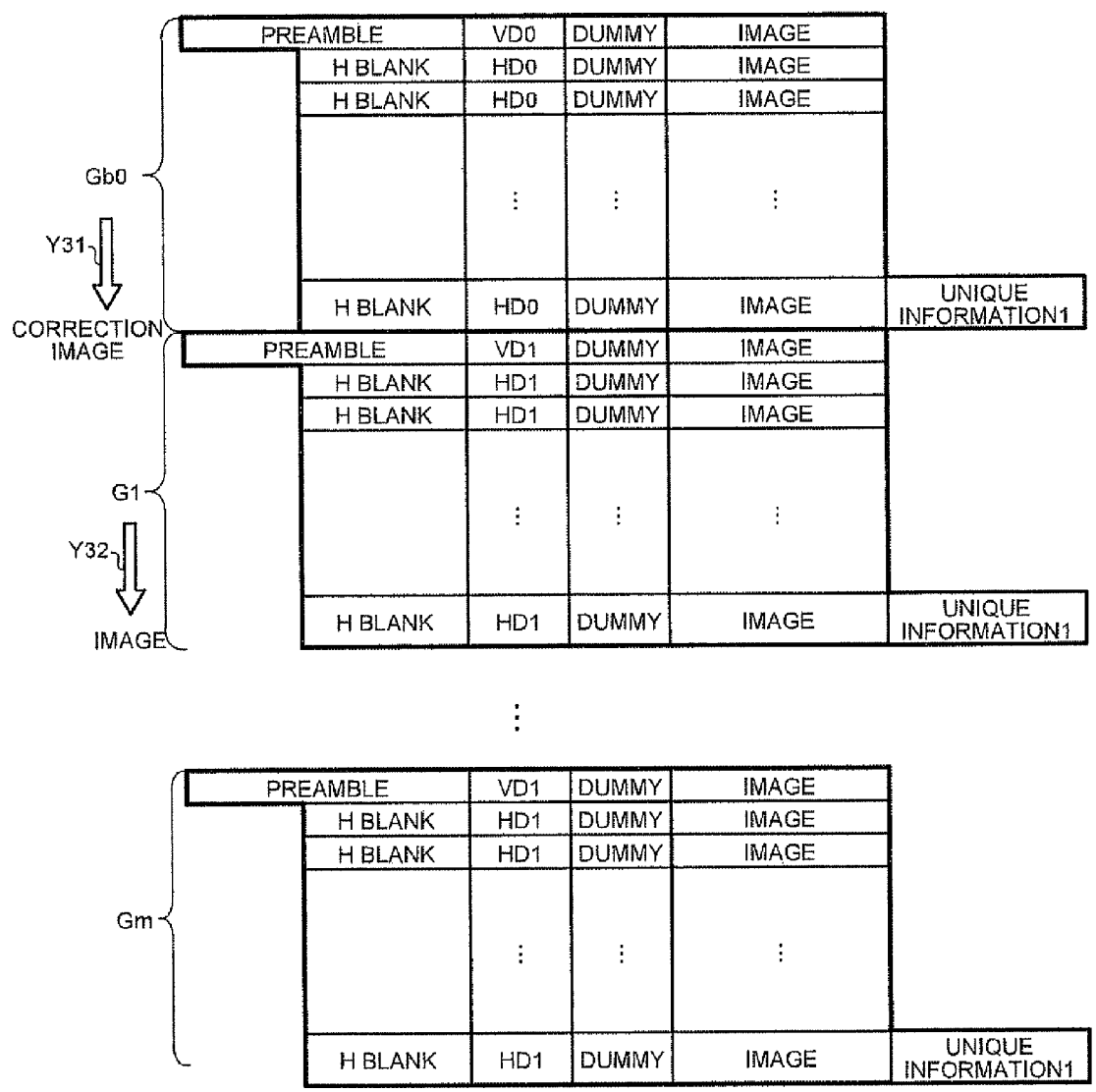
FIG. 12 is an explanatory diagram of the image-signal component transmitted from the capsule endoscope according to the embodiment.

Then, as shown in FIG. 12, the capsule endoscope transmits each scan-line data of a correction image Gb0 using VD0 or HD0 corresponding to the correction image as a synchronization signal. As shown by an arrow Y31, the receiving apparatus can identify that each received scan-line data forms the correction image Gb0 captured by the capsule endoscope by detecting the synchronization signal VD0 or HD0 of each scan-line data. Further, the capsule endoscope transmits each scan-line data of an image G1, which is an ordinary observation image, using VD1 or HD1 as the synchronization signal. As shown by an arrow Y32, the image processing unit in the receiving apparatus can identify that each received scan-line data forms the ordinary observation image G1 captured by the capsule endoscope by detecting the synchronization signal VD1 or HD1 of each scan-line data. The correction image is a fixed pattern image, which is for example a monochrome image or the like captured on a condition that no illumination is used so as to correct sensitivity difference of the CMOS or the like forming the imaging device to temperature. Further, the correction image may be a fixed pattern image for white balance. Further, FIG. 12 describes as an example a case where same unique information 1 is attached to each of images Gb0, G1 to Gm.

Thus, the in-vivo information acquiring system can identify whether each received scan-line data corresponds to each scan-line data for the observation image or for the correction image even when the in-vivo information acquiring system does not properly receive all transmitted data due to a transmission error which occurs during the transmission of image data, whereby the image as a whole is not regarded as an error, and the in-vivo information acquiring system can acquire transmitted data corresponding to single image.

Naturally, also in the capsule endoscope 2 having plural imaging units, synchronization signals corresponding to the observation image and the correction image may be set for each imaging unit, respectively so that the intended usage of the image can be identified with the imaging unit which captures the image. For example, as shown by a table T3 in FIG. 13, in the first imaging unit 22a, VD1 is set as the VD signal, and HD1 is set as the HD signal for the ordinary observation image while VD01 is set as the VD signal, and HD01 is set as the HD signal for the correction image. Further, in the second imaging unit 22b, VD2 is set as the VD signal, and HD2 is set as the HD signal for the ordinary observation image while VD02 is set as the VD signal, and HD02 is set as the HD signal for the correction image. The table T3 illustrated in FIG. 13 is stored in the storage unit 24 in the capsule endoscope 2, or the storage unit 36 in the receiving apparatus 3.

Figure 14:
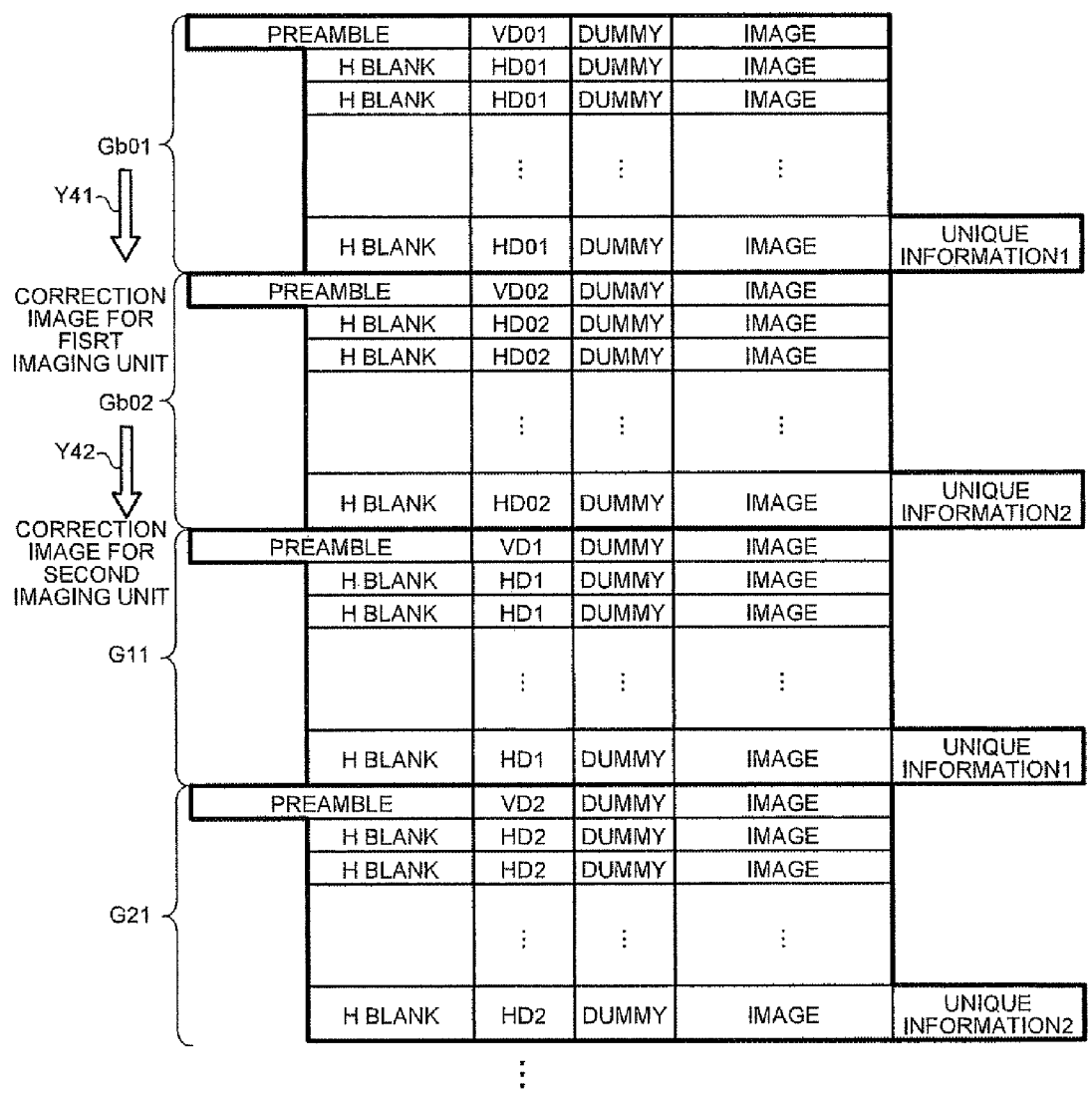
FIG. 14 is an explanatory diagram of another example of the image-signal component transmitted from the capsule endoscope shown in FIG. 1.

In the case above, as shown in FIG. 14, the capsule endoscope 2 transmits each scan-line data of a correction image Gb01 captured by the first imaging unit 22a using VD01 or HD01 corresponding to the correction image captured by the first imaging unit 22a. In the receiving apparatus 3, as shown by an arrow Y41, the image processing unit 34 can identify that each received scan-line data forms the correction image Gb01 for the first imaging unit by detecting the synchronization signal VD01 or HD01 of each scan-line data. Further, the capsule endoscope 2 transmits each scan-line data of a correction image Gb02 of the second imaging unit 22b using VD02 or HD02 corresponding to the correction image of the second imaging unit 22b as the synchronization signal. As shown by an arrow Y42, the receiving apparatus 3 can identify that each received scan-line data forms the correction image Gb02 for the second imaging unit by detecting the synchronization signal VD02 or HD02 of each scan-line data. Further, the capsule endoscope 2 transmits each scan-line data of an image G11, which is an ordinary observation image of the first imaging unit 22a, using VD1 or HD1 corresponding to the ordinary observation image of the first imaging unit 22a as the synchronization signal. Further, the capsule endoscope 2 transmits each scan-line data of an image G021, which is the ordinary observation image of the second imaging unit 22b, using VD2 or HD2 corresponding to the ordinary observation image of the second imaging unit 22b as the synchronization signal. FIG. 14 describes as an example a case where same unique information 1 is attached to the images Gb01, G11 captured by the first imaging unit, and same unique information 2 is attached to the images Gb02, G21 captured by the second imaging unit.

Thus, the in-vivo information acquiring system according to the present embodiment uses the predetermined synchronization signals corresponding to the observation image and the correction image of each imaging unit, respectively so that the in-vivo information acquiring system can identify the image corresponding to each scan-line data by identifying the imaging unit or the intended usage corresponding to each received scan-line data even when the in-vivo information acquiring system does not properly receive all transmitted data due to the transmission error which occurs during the transmission of the image data, whereby the image as a whole is not regarded as an error, and the in-vivo information acquiring system can acquire transmitted data corresponding to single image.

Further, when each imaging unit of the capsule endoscope 2 captures images on one of imaging conditions which differ from each other, a synchronization signal which may be previously set for each imaging condition may be used according to the imaging condition. Then, the storage unit 24 in the capsule endoscope 2 and the storage unit 36 in the receiving apparatus 3 store the synchronization signals which are previously set for each imaging condition used by the capsule endoscope 2. Further, in the capsule endoscope 2, the first signal processing unit 23a, the second signal processing unit 23b, and the communication processing unit 25 transmit scan-line data of an image to be transmitted, using a synchronization signal, of the synchronization signals stored in the storage unit 24, that corresponds to the imaging condition on which the image to be transmitted is captured. Further, in the receiving apparatus 3, the identifying unit 35 in the image processing unit 34 identifies that the image formed by the received scan-line data is captured on the imaging condition corresponding to the synchronization signal, of the synchronization signals stored in the storage unit 36, that is identical with the synchronization signal detected by the synchronizing-signal detection unit 33.

Figure 15:
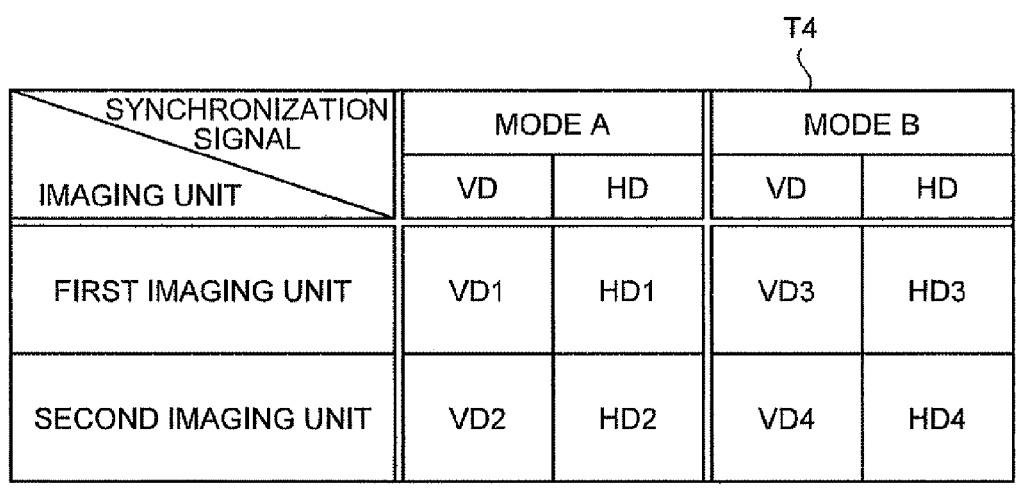
FIG. 15 is a table of illustration of correspondence among each imaging unit, each imaging unit, each imaging mode, and each synchronization signal in the capsule endoscope shown in FIG. 1.

For example, as shown by a table T4 in FIG. 15, in the first imaging unit 22a, VD1 is set as the VD signal and HD1 is set as the HD signal for an image captured on an imaging mode A while VD3 is set as the VD signal and HD3 is set as the HD signal for an image captured on an imaging mode B where a light-adjustment condition or a frame rate is different from that of the imaging mode A. Further, in the second imaging unit 22b, VD2 is set as the VD signal and HD2 is set as the HD signal for an image captured on the imaging mode A while VD4 is set as the VD signal and HD4 is set as the HD signal for an image captured on the imaging mode B.

Figure 16:
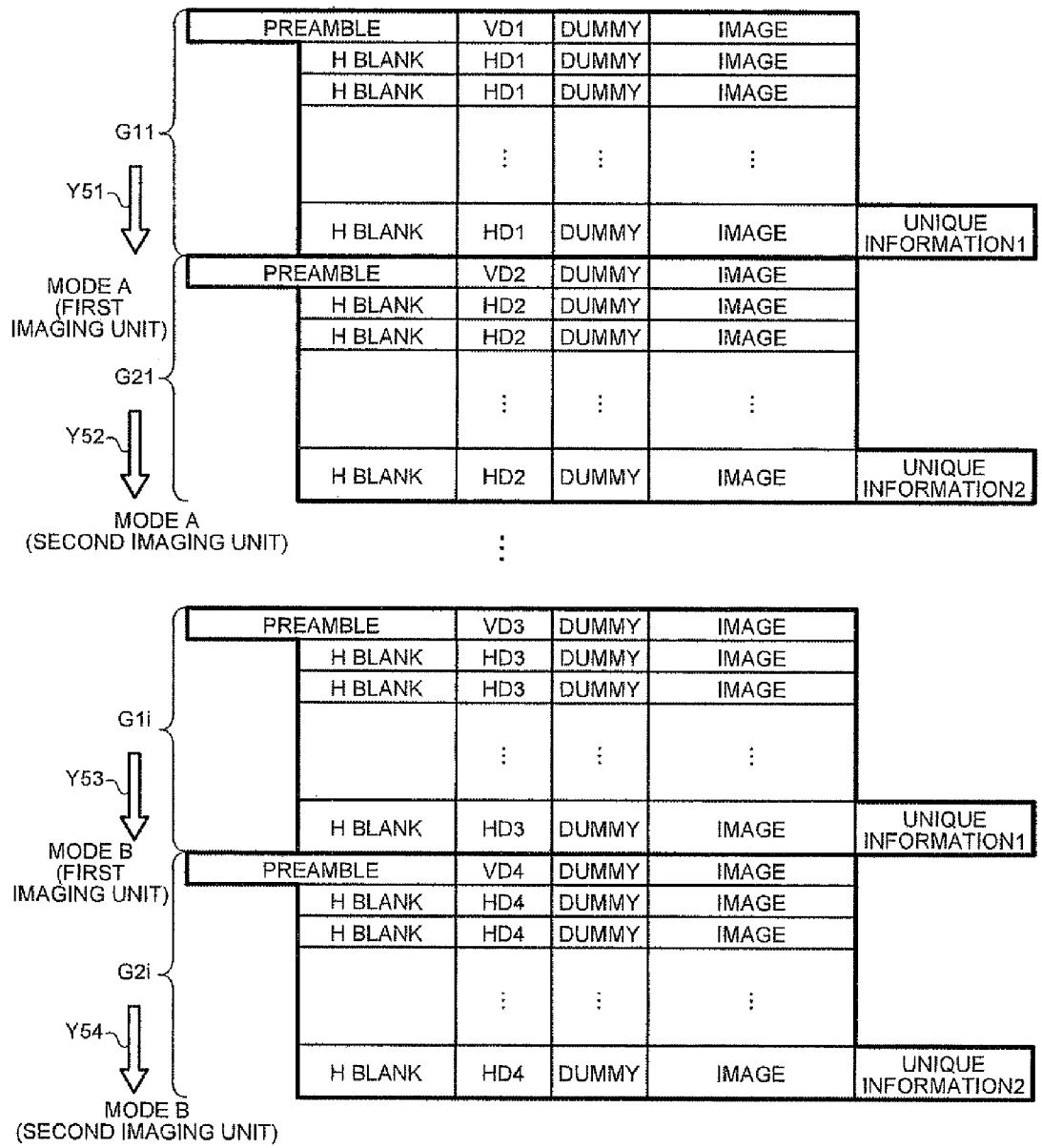
FIG. 16 is an explanatory diagram of another example of the image-signal component transmitted from the capsule endoscope shown in FIG. 1.

In the case above, as shown in FIG. 16, the capsule endoscope 2 transmits each scan-line data of an image G11 captured by the first imaging unit 22a on the imaging mode A using VD1 or HD1 corresponding to the imaging mode A in the first imaging unit 22a as the synchronization signal. As shown by an arrow Y51, the receiving apparatus 3 can identify that each received scan-line data forms the image G11 captured by the first imaging unit 22a on the imaging mode A by detecting the synchronization signal VD1 or HD1 of each scan-line data. Further, the capsule endoscope transmits each scan-line data of an image G21 captured by the second imaging unit 22b on the imaging mode A using VD2 or HD2 corresponding to the imaging mode A in the second imaging unit 22b as the synchronization signal. As shown by an arrow Y52, the receiving apparatus 3 can identify that each received scan-line data forms the image G21 captured by the second imaging unit 22b on the imaging mode A by detecting the synchronization signal VD2 or HD2 of each scan-line data.

Further, the capsule endoscope 2 transmits each scan-line data of an image G1i captured by the first imaging unit 22a on the imaging mode B using VD3 or HD3 corresponding to the imaging mode B in the first imaging unit 22a as the synchronization signal. As shown by an arrow Y53, the receiving apparatus 3 can identify that each received scan-line data forms the image G1i captured by the first imaging unit 22a on the imaging mode B by detecting the synchronization signal VD3 or HD3 of each scan-line data. Further, the capsule endoscope 2 transmits each scan-line data of an image G2i captured by the second imaging unit 22b on the imaging mode B using VD4 or HD4 corresponding to the imaging mode B in the second imaging unit 22b as the synchronization signal. As shown by an arrow Y54, the receiving apparatus 3 can identify that each received scan-line data forms the image G2i captured by the second imaging unit 22b on the imaging mode B by detecting the synchronization signal VD4 or HD4 of each scan-line data. The image processing unit 34 or the image display unit 4 may perform an image processing on each image based on the imaging condition such as the light-adjustment condition of each identified image. Further, FIG. 16 describes as an example a case where the same unique information 1 is attached to the images G11 to G1i captured by the first imaging unit while the same unique information 2 is attached to the images G21 to G2i captured by the second imaging unit.

Thus, the in-vivo information acquiring system according to the present embodiment uses the synchronization signals corresponding to each imaging condition of each imaging unit for the imaging units, respectively so that the in-vivo information acquiring system can identify the image corresponding to each scan-line data by identifying the imaging unit and the imaging condition corresponding to each received scan-line data even when the in-vivo information acquiring system does not properly receive all transmitted data due to the transmission error which occurs during the transmission of the image data, whereby the image as a whole is not regarded as an error, and the in-vivo information acquiring system can acquire transmitted data corresponding to single image. The capsule endoscope 2 may switch the imaging mode not only when the predetermined time elapses, but also when an image of a predetermined feature such as bleeding is detected. The capsule endoscope 2 may change the switching mode depending on a detection value detected by a pH sensor or the like built into the capsule endoscope 2. Further, the capsule endoscope 2 may switch the imaging mode when a signal of an instruction to change the imaging mode that is transmitted from an external apparatus is received.

Further, in the present embodiment, signal constellations of each synchronization signal may be previously set for combinations of one or more imaging units included in the capsule endoscope, one or more intended usages of images, and/or, one or more imaging conditions, respectively. The storage unit in the capsule endoscope and the storage unit in the receiving apparatus stores synchronization signals which are previously set for combinations of one or more imaging units included in the capsule endoscope, one or more intended usages of images, and/or one or more imaging conditions, respectively. Further, in the capsule endoscope, the signal processing unit and the communication processing unit transmits scan-line data of an image to be transmitted using the synchronization signal, of the synchronization signals stored in the storage unit, that corresponds to the imaging unit, the intended usage of images, and/or the imaging condition of the image to be transmitted. Further, in the receiving apparatus, the image processing unit identifies that the image formed by the received scan-line data is captured by the imaging unit, for the intended usage of images, and/or on the imaging condition, which are identical with the synchronization signal, of the synchronization signals stored in the storage unit, that is identical with the synchronization signal detected by the synchronizing-signal detection unit.

For example, as shown by a table T5 in FIG. 17, VD1 to VD12 and HD1 to HD12 are set as the each VD signal and each HD signal for each combination of a light-adjustment condition C or a light-adjustment condition D, and frame rates a, b, or c. The capsule endoscope 2 may transmit scan-line data of an image using the VD signal or the HD signal corresponding to the imaging unit which has captured the image, the light-adjustment condition of the image, and the frame rate of the image. In the receiving apparatus 3, the image processing unit 34 may generate image information from the scan-line data by identifying the imaging unit, the light-adjustment condition, and the frame rate corresponding to the scan-line data based on the synchronization signal of each scan-line data.

Further, the area for the synchronization signals in the scan-line data may be divided into plural areas, and the synchronization signal with the signal constellation corresponding to the imaging unit which has captured the image, the synchronization signal with the signal constellation corresponding to the intended usage of the image, and the synchronization signal with a signal constellation corresponding to the imaging condition of the image may be included in one of the areas, respectively.

As shown in FIG. 18, when the capsule endoscope 2 transmits information of the image captured by the first imaging unit 22a on the imaging mode A, the capsule endoscope 2 may transmit scan-line data L11-k where the HD area is divided into two areas, and HD1 corresponding to the first imaging unit 22a is included in one of the areas while HDA corresponding to the imaging mode A is included the other area. In the receiving apparatus 3, the image processing unit 34 can identify that the scan-line data L11-k is the scan-line data of the image captured by the first imaging unit 22a on the imaging mode A based on HD1 and HDA included in the scan-line data L11-k. Further, as shown in FIG. 19, when the capsule endoscope 2 transmits information of the image captured by the first imaging unit 22a on the light-adjustment condition C with frame rate a, the capsule endoscope 2 may transmit scan-line data L11-j where the HD area is divided into three areas which include HD1 corresponding to the first imaging unit 22a, HDC corresponding to the light-adjustment condition C, and HDa corresponding to the frame rate a. In the receiving apparatus 3, the image processing unit 34 can identify that the scan-line data L11-j is the scan-line data of the image captured by the first imaging unit 22a on the light-adjustment condition C, and with the frame rate a based on HD1, HDC, and HDa included in the scan-line data L11-j.

Further, in the present embodiment, a case where the scan-line data is transmitted with the unique information such as the white balance of the image attached to the end of the last scan-line data is described. The unique information, however, may be separated from the last scan-line data, and transmitted as one line after the last scan-line data is transmitted. In this case, the storage unit 24 in the capsule endoscope 2 and the storage unit 36 in the receiving apparatus 3 store predetermined synchronization signals which indicate the unique information of each imaging unit. In the capsule endoscope 2, the first signal processing unit 23a, the second signal processing unit 23b, and the communication processing unit 25 transmit, separately from the scan-line data of the image, the unique information to be transmitted using the synchronization signal, of the synchronization signals stored in the storage unit 24, that corresponds to the unique information to be transmitted. In the receiving apparatus 3, the synchronizing-signal detection unit 33 detects the synchronization signal from the received information, and the image processing unit 34 identifies that the received information includes the unique information when the synchronization signal detected by the synchronizing-signal detection unit 33 is identical with the synchronization signal indicating the unique information. The image processing unit 34 or the display apparatus 4 performs processes such as a white balance adjustment on the image information corresponding to the unique information based on the unique information.

A case where the unique information 1 of the first imaging unit 22a in the capsule endoscope 2 is transmitted is described below with reference FIG. 20. In the capsule endoscope 2, the first signal processing unit 23a processes the unique information 1 of the first imaging unit 22a into a signal format similar to that of each scan-line data L11i-2 to L11i-n of an image G11i. Specifically, the first signal processing unit 23a sets ID1 which is identical and which indicates the unique information of the first imaging unit 22a as the synchronization signal similarly to each scan-line data L11i-2 to L11i-n of the image G11i to thereby generate identification data L11i-id which includes an H blank signal and a dummy signal along with the unique information 1. The communication processing unit 25 transmits each scan-line data L11i-1 to L11i-n of the image G11i, and then transmits the identification data L11i-id corresponding to the unique information 1 via the antenna 25a. In the receiving apparatus 3, the image processing unit 34 can identify that the identification data L11i-id includes the unique information 1 of the first imaging unit 22a based on the synchronization signal ID1 of the scan-line data L11i-id.

Similarly, in a case where the unique information 2 of the second imaging unit 22b in the capsule endoscope 2 is transmitted, the second signal processing unit 23b sets ID2 which is identical and which indicates the unique information of the second imaging unit 22b as the synchronization signal to generate the identification data L21i-id which includes H blank signal and the dummy signal along with the unique information 2 similarly to each scan-line data L21i-2 to L21i-n of an image G21i so that the unique information 2 of the format of the second imaging unit 22b becomes identical with that of each scan-line data L21i-2 to L21i-n. The communication processing unit 25 transmits each scan-line data L21i-1 to L21i-n of the image G21i, and then transmits the scan-line data L21i-id corresponding to the unique information 2 of the second imaging unit 22b via the antenna 25a. In the receiving apparatus 3, the image processing unit 34 can identify that the identification data L21i-id includes the unique information 2 of the second imaging unit 22b based on the synchronization signal ID2 of the identification scan-line data L21i-id.

Further, since the unique information 1 and 2 include fixed information such as a white balance coefficient, a product serial number, product version information, and product type information, the capsule endoscope needs to transmit the unique information only once instead of every frame. Therefore, when the identification data L11i-id or L21i-id is once transmitted, the capsule endoscope 2 may transmit the scan-line data with the unique information, which is conventionally attached to every frame of the scan-line data, removed therefrom. As a result, a less amount of information is transmitted to the receiving apparatus 3, whereby higher-speed transmission, shortened operation time, and power saving can be achieved.

Further, when the unique information is attached to the scan-line data conventionally, and a transmission or the like occurs in the scan-line data that is the main information part and makes it unable to process the scan-line data, then the unique information attached to the scan-line data is regarded as an error due to the transmission error or the like, and the receiving apparatus cannot acquire the unique information.

Figure 20:
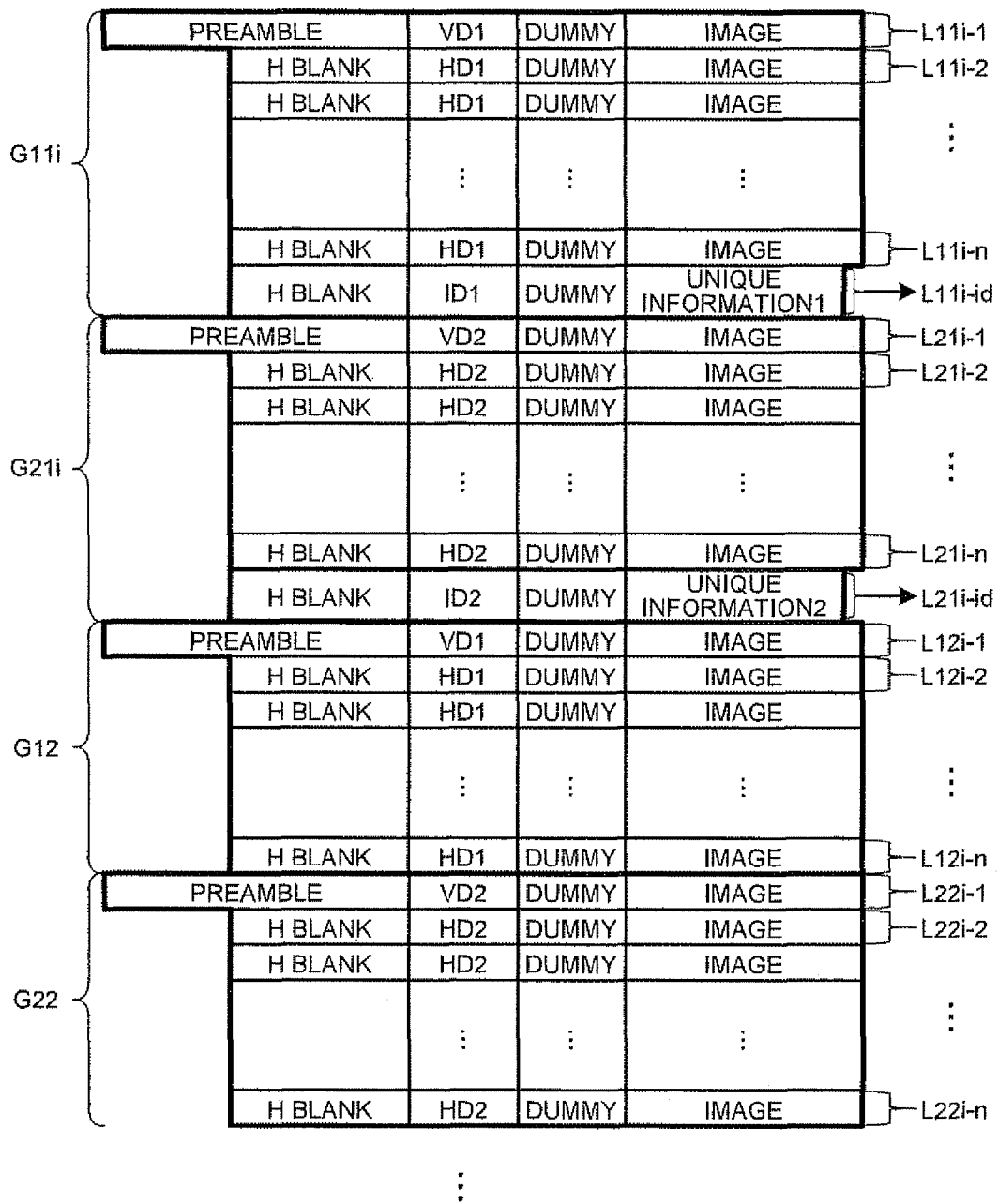
FIG. 20 is an explanatory diagram of another example of the image-signal component transmitted from the capsule endoscope shown in FIG. 1.

On the other hand, in a case shown in FIG. 20, ID1 and ID2 which are identical for the unique information are attached to the unique information as the synchronization signal, and transmitted as the identification data separately from the scan-line data. Therefore, the receiving apparatus 3 can securely acquire the unique information 1, 2 regardless of other scan-line data errors.

Figure 21:
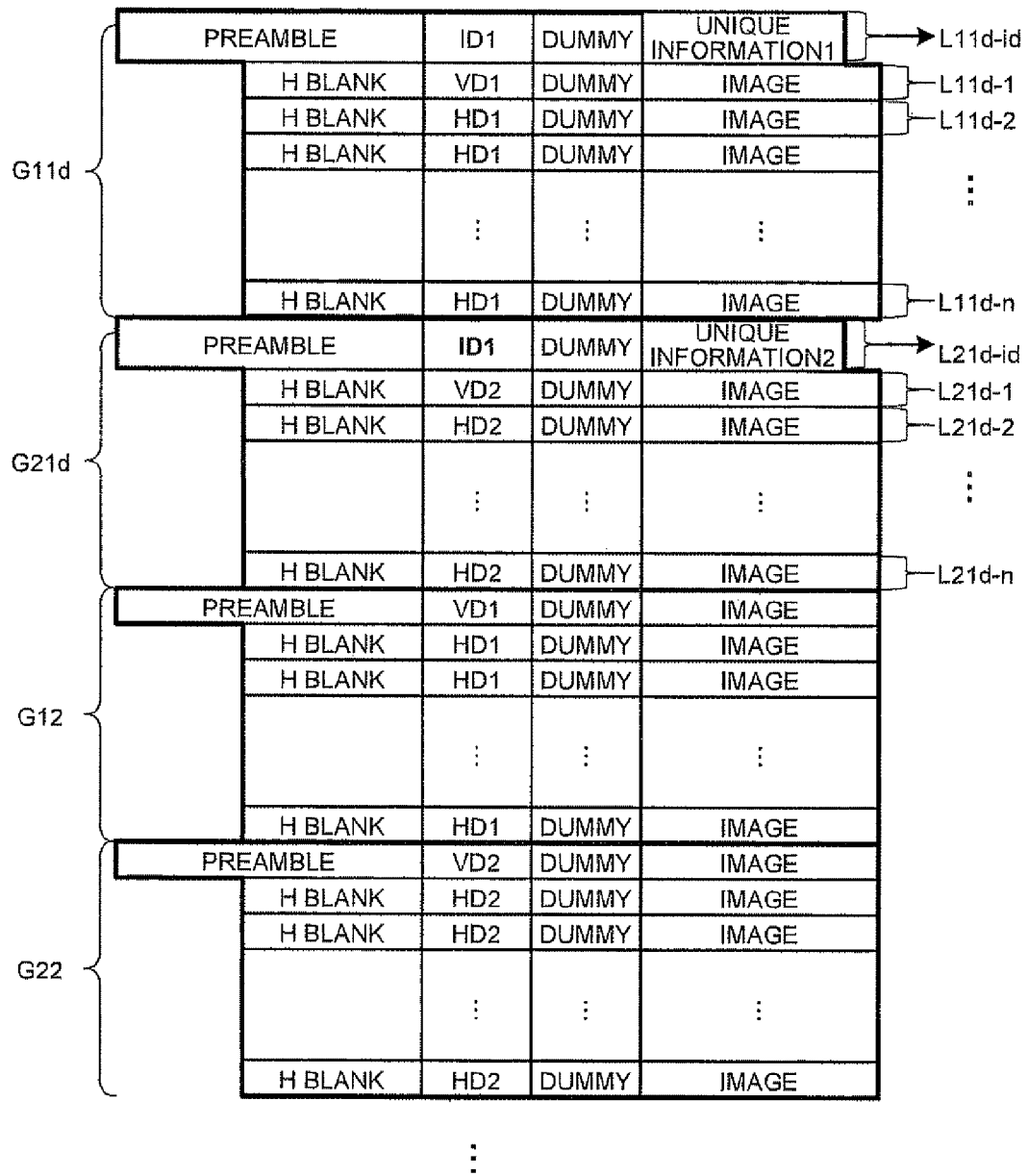
FIG. 21 is an explanatory diagram of another example of the image-signal component transmitted from the capsule endoscope shown in FIG. 1.

Further, as shown in FIG. 21, the capsule endoscope 2 may transmit the identification data corresponding to the unique information of each imaging unit before transmitting the scan-line data of each image. As shown in FIG. 21, in case of the transmission of the unique information 1, the first signal processing unit 23a generates identification data L11d-id where the preamble signal is attached ahead of ID1. The communication processing unit 25 transmits the identification data L11d-id, and then transmits each scan-line data L11d-1 to L11d-n forming an image G11d. Similarly, in case of the transmission of the unique information 2, the second signal processing unit 23b generates identification data L21d-id where the preamble signal is attached ahead of ID2. The communication processing unit 25 transmits the identification data L21d-id, and then transmits each scan-line data L21-2 to L21-n forming an image G21d.

Further, in the present embodiment, a case where the capsule endoscope transmits the scan-line data which is a unit of transmitting image data using the synchronization signal from which the information of the image can be identified is described. The present embodiment, however, is not limited to the case above, and may be applied to a case where the detection result by a sensor built into the capsule endoscope is transmitted. Specifically, the capsule endoscope transmits data including the detection result to be transmitted using the synchronization signal having the signal constellation unique for the sensor so that the transmitted information can be identified as the detection result of a pH sensor or the like. The receiving apparatus detects the synchronization signal in this data and can identify that the receiving data includes the detection result of the sensor in the capsule endoscope.

Thus, in the present embodiment, in the capsule endoscope, the storage unit stores therein the synchronization signals which are previously set for each attached information such as the type of in-vivo information, the imaging unit, the intended usage of images, and the imaging condition of image of in-vivo information which is attached to the in-vivo information such as the image and the detection value of the sensor. The signal processing unit and the communication processing unit acquire the synchronization signal corresponding to the attached information to be attached to the in-vivo information to be transmitted from the synchronization signals stored in the storage unit, and transmit the in-vivo information to be transmitted using the acquired synchronization signal. Further, in the present embodiment, in the receiving apparatus, the storage unit stores therein the synchronization signals which are previously set for each attached information to be attached to the in-vivo information. The synchronizing-signal detection unit detects the synchronization signal from the received information so that the image processing unit can acquire the attached information corresponding to the synchronization signal, of the synchronization signals stored in the storage unit, that is identical with the synchronization signal detected by the synchronizing-signal detection unit, as the attached information of the received in-vivo information. Thus, in the present embodiment, even when the in-vivo information as a whole is not properly acquired due to an information transmission error or the like, the in-vivo information can be acquired by identifying and processing information other than the information where the error occurs with acquisition of the attached information such as the type of the in-vivo information, the imaging unit, the intended usage of images, and the imaging condition of image of the in-vivo information corresponding to the in-vivo information such as the image and the detection value of the sensor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo information acquiring system comprising:
a body-insertable apparatus configured to be introduced inside a subject and to transmit a wireless-transmission signal to an outside of the subject; and
a receiving apparatus configured to receive the wireless-transmission signal transmitted from the body-insertable apparatus,
wherein:
the body-insertable apparatus comprises:
a first imaging unit configured to capture a first image and to output a first image signal based on the captured first image;
a second imaging unit configured to capture a second image and to output a second image signal based on the captured second image;
a transmission-side storage unit configured to store:
a first horizontal synchronizing signal and a first vertical synchronizing signal having a first signal constellation, wherein the first signal constellation identifies the first image signal as being output by the first imaging unit, and
a second horizontal synchronizing signal and a second vertical synchronizing signal having a second signal constellation different from the first signal constellation, wherein the second signal constellation identifies the second image signal as being output by the second imaging unit; and
a transmission unit configured:
to add the first horizontal synchronizing signal and the first vertical synchronizing signal to the first image signal and to transmit a first wireless-transmission signal including the first image signal, the first horizontal synchronizing signal and the first vertical synchronizing signal, and
to add the second horizontal synchronizing signal and the second vertical synchronizing signal to the second image signal and to transmit a second wireless-transmission signal including the second image signal, the second horizontal synchronizing signal and the second vertical synchronizing signal;
the receiving apparatus comprises:
a reception-side storage unit configured to store:
a first relationship associating the first horizontal synchronizing signal and the first vertical synchronizing signal with the first signal constellation identifying the first image signal as being output by the first imaging unit, and
a second relationship associating the second horizontal synchronizing signal and the second vertical synchronizing signal with the second signal constellation identifying the second image signal as being output by the second imaging unit;
a detection unit configured:
to detect the first horizontal synchronizing signal and the first vertical synchronizing signal from the first wireless-transmission signal,
to detect the second horizontal synchronizing signal and the second vertical synchronizing signal from the second wireless-transmission signal; and
a processing unit configured:
to identify the first image signal as being output by the first imaging unit by comparing the first horizontal synchronizing signal and the first vertical synchronizing signal detected by the detection unit with the first relationship stored in the reception-side storage unit, and
to identify the second image signal as being output by the second imaging unit by comparing the second horizontal synchronizing signal and the second vertical synchronizing signal detected by the detection unit with the second relationship stored in the reception-side storage unit,
wherein the transmission unit is configured:
to add the first horizontal synchronizing signal and the first vertical synchronizing signal to the first image signal by:
processing the first image signal into at least a first unit of scan-line data and a second unit of scan-line data,
associating the first vertical synchronizing signal with the first unit of scan-line data of the first image signal, and
associating the first horizontal synchronizing signal with the second unit of scan-line data of the first image signal; and
to add the second horizontal synchronizing signal and the second vertical synchronizing signal to the second image signal by:

processing the second image signal into at least a first unit of scan-line data and a second unit of scan-line data, associating the second vertical synchronizing signal with the first unit of scan-line data of the second image signal, and associating the second horizontal synchronizing signal with the second unit of scan-line data of the second image signal.

2. The in-vivo information acquiring system according to claim 1, wherein the body-insertable apparatus comprises an imaging unit which captures an observation image for observing an inside of the subject and a correction image for correcting the observation image, the transmission-side storage unit stores synchronization signals previously set for each of the intended usages of images, the transmission unit transmits scan-line information of an image to be transmitted using a synchronization signal, of the synchronization signals stored in the transmission-side storage unit, which corresponds to the intended usage of the image, the reception-side storage unit stores synchronization signals previously set for each of the intended usages of images, the detection unit detects the intended usage from the received scan-line information, and the processing unit acquires the intended usage corresponding to a synchronization signal, of the synchronization signals stored in the reception-side storage unit, which is identical with the synchronization signal detected by the detection unit as the intended usage of the image formed by the received scan-line information.

3. The in-vivo information acquiring system according to claim 1, wherein the body-insertable apparatus comprises an imaging unit which captures an image using one of imaging conditions that differ from each other, the transmission-side storage unit stores synchronization signals previously set for each of the imaging conditions, the transmission unit transmits scan-line information of an image to be transmitted using a synchronization signal, of the synchronization signals stored in the transmission-side storage unit, which corresponds to the imaging condition on which the image is captured, the reception-side storage unit stores synchronization signals previously set for each of the imaging conditions in the body-insertable apparatus;

the detection unit detects the synchronization signal from the received scan-line information; and the processing unit identifies that the image formed by the received scan-line information is captured on the imaging condition corresponding to a synchronization signal, of the synchronization signals stored in the reception-side storage unit, that is identical with the synchronization signal detected by the detection unit.

4. The in-vivo information acquiring system according to claim 1, wherein the transmission-side storage unit stores a synchronization signal previously set for each combination of one or more imaging units, one or more intended usages of images, and/or one or more imaging conditions in the body-insertable apparatus, the transmission unit transmits scan-line information of an image to be transmitted using a synchronization signal, of the synchronization signals stored in the transmission-side storage unit, which corresponds to the imaging unit, the intended usage of images, and/or the imaging condition, the reception-side storage unit stores synchronization signals previously set for each combination of one or more imaging units, one or more intended usages of images, and/or one or more imaging conditions in the body-insertable apparatus, the detection unit detects the synchronization signal from the received scan-line information, and the processing unit identifies that the image formed by the received scan-line information is captured by the imaging unit, for the intended use of image, or on the imaging condition corresponding to a synchronization signal, of the synchronization signals stored in the reception-side storage unit, which is identical with the synchronization signal detected by the detection unit.

* * * * *